(12) United States Patent
Aguirre et al.

(10) Patent No.: US 6,428,958 B1
(45) Date of Patent: Aug. 6, 2002

(54) IDENTIFICATION OF CONGENITAL STATIONARY NIGHT BLINDNESS IN DOGS

(75) Inventors: Gustavo D. Aguirre, Ithaca, NY (US); Gregory M. Acland, Kennett Square, PA (US); Kunal Ray, Calcutta (IN)

(73) Assignee: Cornell Research Foundation, Inc., Ithaca, NY (US)

(*) Notice: Subject to any disclaimer, the term of this patent is extended or adjusted under 35 U.S.C. 154(b) by 113 days.

(21) Appl. No.: 09/645,370

(22) Filed: Aug. 24, 2000

Related U.S. Application Data

(62) Division of application No. 09/385,259, filed on Aug. 30, 1999, now Pat. No. 6,201,114.
(60) Provisional application No. 60/103,219, filed on Oct. 6, 1998.

(51) Int. Cl.[7] .............................. C12Q 1/68; C12Q 1/00; C07H 21/02; C07H 21/04
(52) U.S. Cl. .............................. 435/6; 435/4; 536/23.5; 536/23.1; 536/24.3; 536/24.31
(58) Field of Search ........................ 435/4, 6; 536/23.1, 536/23.5, 24.3, 24.31

(56) References Cited

U.S. PATENT DOCUMENTS 5,705,380 A   1/1998   North et al. ............. 435/240.2

OTHER PUBLICATIONS

Aguirre et al., "Congenital Stationary Night Blindness in the Dog: Common Mutation in the RPE65 Gene Indicates Founder Effect," *Molecular Vision* 4:23–29 (1998).
Veske et al., "Retinal Dystrophy of Swedish Briard/Briard–Beagle Dogs is Due to a 4–bp Deletion in RPE65," *Genomics* 57:57–61 (1999).
Wrigstad et al., "Ultrastructural Changes of the Retina and the Retinal Pigment Epithelium in Briard Dogs with Hereditary Congenital Night Blindness and Partial Day Blindness," *Experimental Eye Research* 55:805–808 (1992).
Veske et al., "Isolation of Canine Retinal Arrestin cDNA and Exclusion of Three Candidate Genes for Swedish Briard Retinal Dystrophy," *Current Eye Research* 16:270–274 (1997).
Veske et al., "Organization of the canine Gene Encoding the E Isoform of Retinal Guanylate Cyclase (cGC–E) and Exclusion of its Involvement in the Inherited Retinal Dystrophy of the Swedish Briard and Briard–Beagel Dogs," *Biochimica et Biophysica Acta* 1372:69–77 (1998).
Ray et al., "Strategies for Identification of Mutations Causing Hereditary Retinal Diseases in Dogs: Evaluation of Opsin as a Candidate Gene," *The Journal of Heredity*, 90:133–137 (1999).
Petersen–Jones, "Animal Models of Human Retinal Dystrophies," *Eye* 12:566–570 (1998).
Stades, "Hereditary Features of Progressive Retinal Atrophy (PRA) and its Consequences in Dog–Breeding," *tijdschrift voor diergeneeskunde* 107:29–32 (1982).
Wolf et al., "Rod–Cone Dysplasia in the Collie," *Journal of the American Veterinary Medical Association* 173:1331–1333 (1978).
O Toole et al., "Generalized Progressive Retinal Atrophy in Two Akita Dogs," *Vet. Pathol.* 21:457–462 (1984).
Bjerkás et al., "Progressive Retinal Atrophy in the Tibetan Spaniel in Norway and Sweden," *Veterinary Record* 134:377–379 (1994).
Acland et al., "XLPRA: A Canine Retinal Degeneration Inherited as an X–Linked Trait," *American Journal of Medical Genetics* 52:27–33 (1994).
Kylmä et al., "Cloning and Analysis of the cDNA Encoding the Rod G–Protein Transducin $\alpha$, $\beta 1$ and $\gamma 1$ Subunits From the Canine Retina," *Gene* 193:1–4 (1997).
Acland et al., "Canine familiaris Retinal Pigment Epithelium–Specific Protein RPE65 (RPE65) nRNA," Genbank Accession Number AF084537 (1998).
Veske, "Canis Familiaris mRNA for Retinal Pigment Epithelium Abundant Protein," Genbank Direct Submission. Accession Number Y16567 (1998).
Nicoletti et al., "Molecular Characterization of the Human Gene Encoding an Abundant 61 kDa Protein Specific to the Retinal Pigment Epithelium," *Human Molecular Genetics* 4(4):641–649 (1995).
Han et al., "Characterization of the Structure and Function of a Novel MAP Kinase Kinase (MKK6)," *The Journal of Biological Chemistry* 271(6):2886–2891 (1996).
Ronai et al., "Identification of an ETS–Like 30 kDa Protein that is Expressed in Mammary Tumors Induced by Anti–Benzol(C)phenantrene–3,4–diol–1,2–epoxide," Genbank Direct Submission. Accession Number U30169 (1998).

*Primary Examiner*—Scott D. Priebe
*Assistant Examiner*—Shin-Lin Chen
(74) *Attorney, Agent, or Firm*—Nixon Peabody LLP

(57) ABSTRACT

The present invention relates to an isolated nucleic acid molecule encoding canine RPE65. The present invention also relates to an isolated nucleic acid molecule encoding canine RPE65 having a mutation in one or both alleles indicative of a carrier of or a dog affected with congenital stationary night blindness. The present invention also relates to a method for identifying dogs which are genetically normal, are carriers of, or are affected with congenital stationary night blindness, said method including obtaining a biological sample from a dog and testing the biological sample for a gene encoding canine RPE65 having a nucleic acid mutation in one or both alleles indicative of a carrier of or a dog affected with congenital stationary night blindness. Another aspect of the present invention relates to a method for selecting dogs for breeding.

17 Claims, 5 Drawing Sheets

A
```
   1                                                    cgaccgtctgtcctgccctgggagaca
       Met Ser Ile Gln Val Glu His Pro Ala Gly Gly Tyr Lys Lys Leu Phe Glu Thr Val Glu    20
  28   ATG TCC ATC CAA GTG GAG CAT CCC GCC GGC GGT TAC AAG AAG CTG TTT GAA ACC GTG GAA
       Glu Leu Ser Ser Pro Leu Thr Ala His Val Thr Gly Arg Ile Pro Leu Trp Leu Thr Gly    40
  88   GAG CTG TCG TCG CCG CTC ACC GCC CAC GTG ACA GGC AGG ATC CCG CTC TGG CTC ACG GGC
       Ser Leu Leu Arg Cys Gly Pro Gly Leu Phe Glu Val Gly Ser Glu Pro Phe Tyr His Leu    60
 148   AGT CTC CTC CGA TGC GGA CCG GGG CTC TTC GAG GTT GGA TCT GAA CCA TTT TAC CAC CTG
       Phe Asp Gly Gln Ala Leu Leu His Lys Phe Asp Phe Lys Glu Gly His Val Thr Tyr His    80
 208   TTT GAC GGA CAA GCC CTT CTG CAC AAG TTC GAC TTT AAA GAA GGA CAC GTC ACC TAT CAC
       Arg Arg Phe Ile Arg Thr Asp Ala Tyr Val Arg Ala Met Thr Glu Lys Arg Ile Val Ile   100
 268   AGA AGG TTC ATC CGC ACC GAT GCT TAC GTC CGG GCA ATG ACC GAG AAA AGG ATC GTC ATA
       Thr Glu Phe Gly Thr Cys Ala Phe Pro Asp Pro Cys Lys Asn Ile Phe Ser Arg Phe Phe   120
 328   ACG GAA TTT GGC ACC TGT GCG TTC CCA GAT CCC TGC AAG AAT ATA TTT TCC AGG TTT TTT
       Ser Tyr Phe Arg Gly Val Glu Val Thr Asp Asn Ala Leu Val Asn Val Tyr Pro Val Gly   140
 388   TCT TAC TTC CGA GGA GTG GAG GTC ACT GAC AAT GCC CTT GTT AAC GTC TAC CCA GTA GGG
       Glu Asp Tyr Tyr Ala Cys Thr Glu Thr Asn Phe Ile Thr Lys Ile Asn Pro Glu Thr Leu   160
 448   GAA GAT TAC TAC GCC TGC ACG GAG ACC AAC TTC ATT ACA AAG ATT AAT CCT GAG ACC CTG
       Glu Thr Ile Lys Gln Val Asp Leu Cys Asn Tyr Val Ser Val Asn Gly Ala Thr Ala His   180
 508   GAG ACA ATT AAG CAG GTT GAT CTC TGC AAT TAC GTC TCT GTC AAT GGA GCC ACC GCT CAC
       Pro His Ile Glu Asn Asp Gly Thr Val Tyr Asn Ile Gly Asn Cys Phe Gly Lys Asn Phe   200
 568   CCC CAC ATT GAA AAT GAT GGG ACT GTT TAC AAC ATT GGT AAT TGC TTT GGG AAA AAT TTT
       Ser Ile Ala Tyr Asn Ile Val Lys Ile Pro Pro Leu Gln Ala Asp Lys Glu Asp Pro Ile   220
 628   TCG ATT GCC TAC AAT ATT GTA AAG ATC CCT CCA CTC CAA GAC AAG GAA GAT CCA ATA
       Ser Lys Ser Glu Val Val Val Gln Phe Pro Cys Ser Asp Arg Phe Lys Pro Ser Tyr Val   240
 688   AGC AAG TCC GAG GTC GTC GTA CAA TTC CCC TGC AGC GAC CGA TTC AAG CCA TCG TAC GTC
       His Ser Phe Gly Leu Thr Pro Asn Tyr Ile Val Phe Val Glu Thr Pro Val Lys Ile Asn   260
 748   CAT AGT TTT GGT TTG ACT CCC AAC TAT ATT GTT TTT GTG GAG ACG CCA GTC AAA ATT AAC
       Leu Leu Lys Phe Leu Ser Ser Trp Ser Leu Trp Gly Ala Asn Tyr Met Asp Cys Phe Glu   280
 808   CTG CTC AAG TTC CTT TCT TCG TGG AGT CTT TGG GGA GCC AAC TAC ATG GAT TGT TTT GAG
       Ser Asn Glu Thr Met Gly Val Trp Leu His Ile Ala Asp Lys Lys Arg Lys Lys Tyr Leu   300
 868   TCC AAT GAA ACC ATG GGG GTT TGG CTT CAC ATC GTC GAC AAA AAA AGA AAA AAG TAT CTC
       Asn Asn Lys Tyr Arg Thr Ser Ser Phe Asn Leu Phe His His Ile Asn Thr Tyr Glu Asp   320
 928   AAT AAT AAG TAC AGG ACC TCT TCC TTT AAT CTC TTC CAT CAT ATC AAT ACT TAC GAA GAC
       Asn Glu Phe Leu Ile Val Asp Leu Cys Cys Trp Lys Gly Phe Glu Phe Val Tyr Asn Tyr   340
 988   AAT GAG TTT CTG ATT GTG GAT CTC TGC TGC TGG AAA GGA TTT GAA TTC GTC TAC AAT TAC
       Leu Tyr Leu Ala Asn Leu Arg Glu Asn Trp Glu Glu Val Lys Lys Asn Ala Arg Lys Ala   360
1048   TTG TAT TTA GCC AAT TTA CGT GAG AAC TGG GAA GAG GTG AAA AAA AAT GCC AGA AAG GCT
       Pro Gln Pro Glu Val Arg Arg Ser Val Leu Pro Leu Asn Ile Asp Lys Ala Asp Thr Gly   380
1108   CCG CAG CCT GAA GTT AGG AGA TCC GTG CTT CCT TTG AAT ATC GAC AAG GCC GAC ACA GGC
       Lys Asn Leu Val Thr Leu Pro Asn Thr Thr Ala Thr Ala Thr Leu Arg Ser Asp Glu Thr   400
1168   AAG AAC CTA GTC ACC CTT CCC AAC ACG ACG GCC ACT GCA ACT CTG CGC AGC GAC GAG ACC
       Ile Trp Leu Glu Pro Glu Val Leu Phe Ser Gly Pro Arg Gln Ala Phe Glu Phe Pro Gln   420
1228   ATC TGG CTG GAA CCT GAG GTT CTC TTC TCA GGG CCT CGT CAA GCC TTT GAG TTT CCT CAA
       Ile Asn Tyr Gln Lys Tyr Gly Gly Lys Pro Tyr Thr Tyr Ala Tyr Gly Leu Gly Leu Asn   440
1288   ATC AAC TAT CAG AAG TAT GGC GGG AAG CCT TAC ACG TAC GCG TAT GGA CTT GGC TTG AAT
       His Phe Val Pro Asp Arg Leu Cys Lys Leu Asn Val Lys Thr Lys Glu Thr Trp Val Trp   460
1348   CAC TTC GTT CCG GAC AGG CTC TGC AAG CTG AAC GTC AAA ACT AAA GAA ACG TGG GTA TGG
       Gln Glu Pro Asp Ser Tyr Pro Ser Glu Pro Ile Phe Val Ser His Pro Asp Ala Leu Glu   480
1408   CAA GAG CCC GAC TCA TAC CCA TCA GAA CCC ATC TTT GTT TCT CAC CCA GAT GCC TTG GAA
       Glu Asp Asp Gly Val Val Leu Ser Val Val Val Ser Pro Gly Ala Gly Gln Lys Pro Ala   500
1468   GAA GAT GAT GGT GTA GTT CTG AGT GTG GTG GTG AGC CCT GGG GCA GGA CAA AAG CCT GCT
       Tyr Leu Leu Ile Leu Asn Ala Lys Asp Leu Ser Glu Val Ala Arg Ala Glu Val Glu Ile   520
1528   TAT CTT CTG ATT CTG AAT GCC AAG GAT TTG AGT GAA GTT GCC AGG GCT GAA GTG GAG ATT
       Asn Ile Pro Val Thr Phe His Gly Leu Phe Lys Lys Ser *                              533
1588   AAC ATC CCT GTC ACC TTT CAT GGA CTG TTC AAA AAA TCC TAA gtacattctagcaaattatattt
1653   ctattgacaaagtcaagaaaaagtgaggtctgcaatcaaattctgttcaattttagcctgctgtattacagg
```

B
```
   1   Met Ser Ile Gln Val Glu His Pro Ala Gly Gly Tyr Lys Lys Leu Phe Glu Thr Val Glu    20
  21   Glu Leu Ser Ser Pro Leu Thr Ala His Val Thr Gly Arg Ile Pro Leu Trp Leu Thr Gly    40
  41   Ser Leu Leu Arg Cys Gly Pro Gly Leu Phe Glu Val Gly Ser Glu Pro Phe Tyr His Leu    60
  61   Phe Asp Gly Gln Ala Leu Leu His Lys Phe Asp Phe Lys Glu Gly His Val Thr Tyr His    80
  81   Arg Arg Phe Ile Arg Thr Asp Ala Tyr Val Arg Ala Met Thr Glu Lys Arg Ile Val Ile   100
 101   Thr Glu Phe Gly Thr Cys Ala Phe Pro Asp Pro Cys Lys Asn Ile Phe Ser Arg Phe Phe   120
 121   Ser Tyr Phe Arg Gly Val Glu Val Thr Asp Asn Ala Leu Val Asn Val Tyr Pro Val Gly   140
 141   Glu Asp Tyr Tyr Ala Cys Thr Glu Thr Asn Phe Ile Thr Leu Ile Leu Arg Pro Trp Arg   160
 161   Gln Leu Ser Arg Leu Ile Ser Ala Thr Thr Ser Leu Ser Met Glu Pro Pro Leu Thr Pro   180
 181   Thr Leu Lys Met Met Gly Leu Phe Thr Thr Leu Val Ile Ala Leu Gly Lys Ile Phe Arg   200
 201   Leu Pro Thr Ile Leu Stop                                                           205
```

FIGURE 1

IDENTIFICATION OF CONGENITAL STATIONARY NIGHT BLINDNESS IN DOGS

This application is a divisional of U.S. patent application Ser. No. 09/385,259, filed Aug. 30, 1999, now U.S. Pat. No. 6,201,114, which claims the benefit of U.S. Provisional Patent Application Serial No. 60/103,219, filed Oct. 6, 1998.

The subject matter of this application was made with support from the United States Government under Grant No. EY 06855 from the National Institutes of Health. The United States Government may retain certain rights.

FIELD OF THE INVENTION

The present invention relates to the identification of the RPE65 gene in dogs, identification of a mutation in the RPE65 gene in the briard breed of dogs, a method for identifying dogs that are genetically normal, are carriers of, or are affected with congenital stationary night blindness by detecting the presence of the mutation, and a method of selecting dogs for breeding.

BACKGROUND OF THE INVENTION

The briard dog is affected with a recessively inherited retinal disorder characterized by congenital night blindness with various degrees of visual impairment under photopic illumination. Vision in affected dogs ranges from normal day vision to profound day blindness (Narfström et al., "Hereditary Retinal Dystrophy In The Briard Dog: Clinical And Hereditary Characteristics," *Veterinary & Comparative Ophthalmology*, 4:85–92 (1994)). The disease was initially described in Swedish dogs as a stationary disorder analogous to human congenital stationary night blindness (CSNB; Narfström et al., "Hereditary Retinal Dystrophy In The Briard Dog: Clinical And Hereditary Characteristics," *Veterinary & Comparative Ophthalmology*, 4:85–92 (1994)). More recently, the disease has been described as having a progressive component, and has been termed hereditary retinal dystrophy (Wrigstad et al., "Slowly Progressive Changes Of The Retina And Retinal Pigments Epithelium In Briard Dogs With Hereditary Retinal Dystrophy. A Morphologic Study," *Doc. Ophthalmol.*, 87:337–354 (1994); Wrigstad, "Hereditary Dystrophy Of The Retina And The Retinal Pigment Epithelium In A Strain Of Briard Dogs: A Clinical, Morphologic And Electroretinographic Study," Linköping University Medical Dissertation #423 (1994)). Along with the visual impairment, affected dogs have an abnormal electroretinogram (ERG); in general, the recorded responses are normal in waveform, but show a marked diminution of response amplitudes, similar to a "Riggs type" ERG in man. The ERG recorded under DC conditions shows complete absence of the a-, b-, and c-waves, with the latter waveform being replaced by a very slow negative potential which develops when the stimulus intensity is greater than 3 log units above the normal b-wave threshold. The abnormalities in the a- and b-waves can be interpreted as representing a delay in rod phototransduction (Nilsson et al., "Changes In The DC Electroretinogram In Briard Dogs With Hereditary Congenital Night Blindness And Partial Day Blindness," *Exp. Eye Res.*, 54:291–296 (1992)). A similar disease is also recognized in other countries, e.g. France, Canada, and the United States. In the United States, the disease is termed congenital stationary nightblindness, and csnb has been designated as the gene symbol for the disease locus. Apart from the above studies in Swedish briard dogs, no other systematic investigation of the disease has been reported, nor has there been definitive proof that csnb and retinal dystrophy represent the same disorder.

The present invention is directed to overcoming the above-noted deficiencies in the prior art.

SUMMARY OF THE INVENTION

The present invention relates to an isolated nucleic acid molecule encoding canine RPE65.

The present invention also relates to an isolated nucleic acid molecule encoding canine RPE65 having a mutation in one or both alleles indicative of a carrier of or a dog affected with congenital stationary night blindness.

The present invention also relates to a method for identifying dogs which are genetically normal, are carriers of, or are affected with congenital stationary night blindness, said method including obtaining a biological sample from a dog and testing the biological sample for a gene encoding canine RPE65 having a nucleic acid mutation in one or both alleles indicative of a carrier of or a dog affected with congenital stationary night blindness.

Another aspect of the present invention is a method for selecting dogs for breeding which includes obtaining a biological sample from a dog, testing the biological sample for a gene encoding canine RPE65 having a nucleic acid mutation in one or both alleles indicative of a carrier of or a dog affected with congenital stationary night blindness, and eliminating dogs with the mutation from a breeding stock or breeding the dogs with the mutation with genetically normal dogs.

Yet another aspect of the present invention is an isolated nucleic acid molecule including a DNA molecule having the nucleotide sequence selected from the group consisting of SEQ. ID. No. 4, SEQ. ID. No. 5, SEQ. ID. No. 6, SEQ. ID. No. 7, and SEQ. ID. No. 8.

The present invention has enabled a DNA-based diagnostic test for congenital stationary night blindness to be developed, and, therefore, animals suitable for breeding can be identified. In particular, identifying carriers for congenital stationary night blindness through the identification of the AAGA deletion mutation at nucleotides 487–490 in a gene encoding canine RPE65 allows a breeder to eliminate the carriers from the breeding stock or breed carriers with genetically normal dogs.

BRIEF DESCRIPTION OF THE DRAWINGS

FIGS. 1A–1B: FIG. 1A shows the nucleotide (cDNA) and deduced amino acid sequences of canine RPE65 (wildtype allele) Nucleotides 487–490 (AAGA)=sequence deleted in mutant allele. Nucleotides 417–442, and 523–499=binding sites for primers RPE65-1 (forward) and RPE65-3 (reverse), respectively, used to amplify across the mutant site. Amino Acids=codons (225, 262, 308, 322, 368, 395, 397, and 427) that differ from human sequences. Start (Met) and Stop (*) Codons=nucleotides 28–30 and 1627–9, respectively. Lowercase=5' and 3' UTRs (nucleotides 1–27 and 1630–1725, respectively). FIG. 1B shows the deduced amino acide sequence of canine mutant RPE65. Amino Acids=codons that differ from wildtype sequence.

(FIGS. 3A and 3B×500; FIGS. 3C–D×1250).

DETAILED DESCRIPTION OF THE INVENTION

Figure 2:
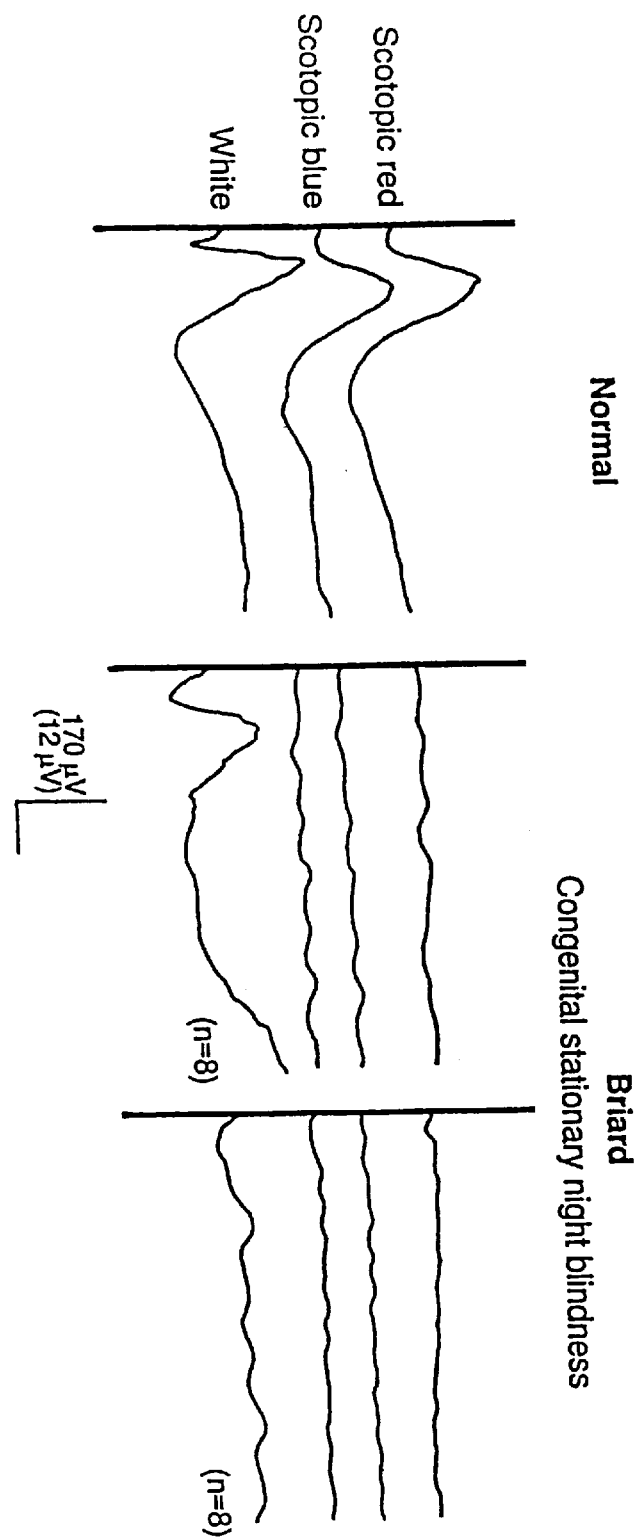
FIG. 2 shows representative dark adapted ERG responses recorded from a normal dog (left) and 2 briard dogs with congenital stationary night blindness ("csnb") (center and right). The normal dog responds to scotopically balanced red and blue light stimuli with responses which are similar in waveform and amplitude. The response to a single high intensity (4.0 log-foot Lamberts) white light stimulus is biphasic, with a prominent a-wave, and an overall shorter latency b-wave response. In contrast, dogs affected with csnb have minute responses which are barely discernible over the baseline noise. When signal averaged over 8 responses (n=8), a distinct ERG response is evident, and the waveform is more characteristic of the normal response in the younger (4 months, center column) than in the older (2 years, right column) animal. This difference is not a characteristic finding with aging. (n=8) is the number of responses averaged; vertical calibration is 170 μV for single responses, and 12 μV for averaged responses; horizontal calibration=50 msec.

The present invention relates to an isolated nucleic acid molecule encoding canine RPE65.

The DNA and amino acid sequences for canine RPE65 are identified in FIGS. 1A and 1B. The wildtype gene sequence for canine RPE65 is provided in SEQ. ID. No. 1 as follows:

cgaccgtctg tcctgccctg ggagacaatg tccatccaag tggagcatcc cgccggcggt 60
tacaagaagc tgtttgaaac cgtggaagag ctgtcgtcgc cgctcaccgc ccacgtgaca 120
ggcaggatcc cgctctggct cacgggcagt ctcctccgat gcggaccggg gctcttcgag 180
gttggatctg aaccatttta ccacctgttt gacggacaag cccttctgca caagttcgac 240
tttaaagaag gacacgtcac ctatcacaga aggttcatcc gcaccgatgc ttacgtccgg 300
gcaatgaccg agaaaaggat cgtcataacg gaatttggca cctgtgcgtt cccagatccc 360
tgcaagaata tattttccag gtttttttct tacttccgag gagtggaggt cactgacaat 420
gcccttgtta acgtctaccc agtaggggaa gattactacg cctgcacgga gacaacttc 480 attacaaaga ttaatcctca gaccctggag acaattaagc aggttgatct ctgcaactac 540
gtctctgtca atggagccac cgctcacccc cacattgaaa atgatgggac tgtttacaac 600
attggtaatt gctttgggaa aaatttttcg attgcctaca atattgtaaa gatccctcca 660
ctccaagcag acaaggaaaa tccaataagc aagtccgagg tcgtcgtaca attcccctgc 720
agcgaccgat tcaagccazc gtacgtccat agttttggtt tgactcccaa ctatattgtt 780
tttgtggaga cgccagtcaa aattaacctg ctcaagttcc tttcttcgtg gagtctttgg 840
ggagccaact acatggattg ttttgagtcc aatgaaacca tgggggtttg gctcacatc 900 gctgacaaaa aagaaaaaa gtatctcaat aataagtaca ggacctcttc cttaatctc 960 ttccatcata tcaatactta cgaagacaat gagtttctga ttgtggatct ctgctgctgg 1020
aaaggatttg aattcgtcta caattacttg tatttagcca atttacgtga gaactgggaa 1080
gaggtgaaaa aaaatgccag aaaggctccg cagcctgaag ttaggagatc cgtgcttcct 1140
ttgaatatcg acaaggccga cacaggcaag aacctagtca cccttcccaa cacgacggcc 1200 actcaactc tgcgcagcga cgagaccatc tggctggaac ctgaggttct cttctcaggg 1260
cctcgtcaag cctttgagtt tcctcaaatc aactatcaga agtatggcgg gaagccttac 1320
acgtacgcgt atggacttgg cttgaatcac ttcgttccgg acaggctctg caagctgaac 1380
gtcaagacta aagaaacgtg ggtatggcaa gagcccgact cataaccate agaacccatc 1440 ttgtttctc acccagatgc cttggaagaa gatgatggtg tagttctgag tgtggtggtg 1500
agccctgggg caggacaaaa gcctgcttat cttctgattc tgaatgccaa ggatttgagt 1560
gaagttgcca gggctgaagt ggagattaac atccctgtca cctttcatgg actgttcaaa 1620 aatcctaag tacattctag caaattatat ttctattgac aaagtcaaga aaaagtgagg 1680
tctgcaatca aattctgt c aattttagcc tgctgtatta cagg 1724

The wildtype amino acid sequence for canine RPE65 is provided in SEQ. ID. No. 2 as follows:

```
Met Ser Ile Gln Val Glu His Pro Ala Gly Gly Tyr Lys Lys Leu Phe
 1               5                  10                  15

Glu Thr Val Glu Glu Leu Ser Ser Pro Leu Thr Ala His Val Thr Gly
                20                  25                  30

Arg Ile Pro Leu Trp Leu Thr Gly Ser Leu Leu Arg Cys Gly Pro Gly
            35                  40                  45

Leu Phe Glu Val Gly Ser Glu Pro Phe Tyr His Leu Phe Asp Gly Gln
        50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
            115                 120                 125

Thr Asp Asn Ala Leu Val Asn Val Tyr Pro Val Gly Glu Asp Tyr Tyr
        130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Val Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Leu Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Ser Phe Asn Leu Phe His His Ile Asn Thr Tyr Glu Asp
305                 310                 315                 320

Asn Glu Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
        340                 345                 350

Val Lys Lys Asn Ala Arg Lys Ala Pro Gln Pro Glu Val Arg Arg Ser
    355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Thr Leu Arg Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Gly Gly Lys Pro Tyr Thr
        420                 425                 430
```

-continued

```
Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530
```

The present invention also provides fragments of the nucleic acid molecules. Fragments of the nucleic acid molecules can be used to hybridize to target nucleic acid molecules to detect the presence of a mutation. The fragments must be long enough to be useful as a primer in a polymerase chain reaction (PCR) process or a probe in a ligase chain reaction (LCR) procedure. Preferred fragments are at least twelve bases in length.

The nucleic acid molecules or fragments need not be identical to the sequence of SEQ. ID. No. 1. Suitable nucleic acid molecules may be identified by hybridization to the nucleic acid sequence of the gene encoding canine RPE65, preferably SEQ. ID. No. 1. In a preferred embodiment, a suitable nucleic acid molecule hybridizes to the nucleic acid sequence of the gene encoding canine RPE65 of SEQ. ID. No. 1 under stringent conditions. For example, sequences can be isolated that hybridize to a DNA molecule comprising a nucleotide sequence of 50 continuous bases of SEQ. ID. No. 1 under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2×SSC buffer at 42° C.

The nucleic acid molecules of the present invention may be linked to other nucleic acid molecules such as vectors or tags to facilitate amplification, purification, or identification.

The present invention also relates to an isolated nucleic acid molecule encoding canine RPE65 having a mutation in one or both alleles indicative of a carrier of or a dog affected with congenital stationary night blindness.

The amino acid sequence of canine mutant RPE65 is provided in SEQ. ID. No. 3 as follows:

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
                20                  25                  30

Arg Ile Pro Leu Trp Leu Thr Gly Ser Leu Leu Arg Cys Gly Pro Gly
            35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
                115                 120                 125

Thr Asp Asn Ala Leu Val Asn Val Tyr Pro Val Gly Glu Asp Tyr Tyr
            130                 135                 140

Ala Cys Thr Glu Thr Asn Phe Ile Thr Leu Ile Leu Arg Pro Trp Arg
145                 150                 155                 160
```

```
-continued

Gln Leu Ser Arg Leu Ile Ser Ala Thr Thr Ser Leu Ser Met Glu Pro
            165                 170                 175

Pro Leu Thr Pro Thr Leu Lys Met Met Gly Leu Phe Thr Thr Leu Val
            180                 185                 190

Ile Ala Leu Gly Lys Ile Phe Arg Leu Pro Thr Ile Leu
        195                 200                 205
```

In a preferred embodiment, an AAGA deletion mutation at nucleotides 487–490 produces a frameshift, causing a deduced mistranslation with a premature stop codon. This type of nucleotide change in the gene sequence is referred to as a disease-causing mutation.

The present invention also provides fragments of the nucleic acid molecules. The nucleic acid molecules or fragments need not be identical to the sequence of SEQ. ID. No. 1, excluding the deletion mutation. Rather the nucleic acid molecule needs to have the deletion mutation and sufficient identity to the remainder of SEQ. ID. No. 1 so that the nucleic acid molecule or fragment may be used to differentiate between genetic material having the mutation and genetic material lacking the mutation.

Suitable nucleic acid molecules may be identified by hybridization to the nucleic acid sequence of the geneencoding canine RPE65, preferably SEQ. ID. No. 1, with an AAGA deletion mutation at nucleotides 487–490, but not hybridization to SEQ. ID. No. 1. In a preferred embodiment, a suitable nucleic acid molecule hybridizes to the nucleic acid sequence of the gene encoding canine RPE65 of SEQ. ID. No. 1 with an AAGA deletion mutation at nucleotides 487–490, but does not hybridize to SEQ. ID. No. 1, under stringent conditions. For example, sequences can be isolated that hybridize to a DNA molecule comprising a nucleotide sequence of 50 continuous bases of SEQ. ID. No. 1 including the AAGA deletion mutation under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2×SSC buffer at 42° C.

The nucleic acid molecules of the present invention may be linked to other nucleic acid molecules such as vectors or tags to facilitate amplification, purification, or identification.

The present invention also relates to a method for identifying dogs, particularly of the briard breed, which are genetically normal, are carriers of, or are affected with congenital stationary night blindness, said method including obtaining a biological sample from a dog and testing the biological sample for a gene encoding canine RPE65 having a nucleic acid mutation in one or both alleles indicative of a carrier of or a dog affected with congenital stationary night blindness.

In a preferred embodiment, the biological sample is any tissue containing genomic DNA. Most preferably, the biological sample is blood, hair, mucosal scrapings, semen, tissue biopsy, or saliva. In a most preferred embodiment, the biological sample is blood.

A gene encoding canine RPE65 having the nucleic acid mutation disclosed in the present invention in one allele is indicative of a carrier of congenital stationary night blindness. A gene encoding canine RPE65 having the nucleic acid mutation disclosed in the present invention in both alleles is indicative of a dog affected with congenital stationary night blindness.

Methods of screening a biological sample for mutated nucleic acids can be carried out using either deoxyribonucleic acids ("DNA") or messenger ribonucleic acids ("mRNA") isolated from the biological sample. During periods when the gene is expressed, mRNA may be abundant and more readily detected. However, these genes are temporally controlled and, at most stages of development, the preferred material for screening is DNA.

Oligonucleotide Ligation Assay ("OLA") (Landegren et el., "A Ligase-Mediated Gene Detection Technique," Science, 241:1077–1080 (1988); Landegren et al., "DNA Diagnostics—Molecular Techniques and Automation," Science, 242:229–237 (1988); U.S. Pat. No. 4,988,617 to Landegren et al., which are hereby incorporated by reference), as described below, is one method for testing the genetic material in the biological sample. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting deletion mutations. However, numerous methods for characterizing or detecting deletion mutations are known in the art and any of those methods are also suitable for the present invention.

Another method of characterizing a deletion mutation entails direct DNA sequencing of the genetic locus that flanks and includes the deletion. Such analysis can be accomplished using either the "dideoxy-mediated chain termination method," also known as the "Sanger Method" (Sanger et al., "DNA Sequencing with Chain-Terminating Inhibitors," Proc. Natl. Acad. Sci. USA, 74:5463–5467 (1977), which is hereby incorporated by reference) or the "chemical degradation method," also known as the "Maxam-Gilbert method" (Maxam et al., "A New Method for Sequencing DNA," Proc. Natl. Acad. Sci. USA, 74:560–564 (1977), which is hereby incorporated by reference).

One example of a procedure for sequencing DNA molecules using arrays of oligonucleotides is disclosed in U.S. Pat. No. 5,202,231 to Drmanac et at., which is hereby incorporated by reference. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also Chetverin et al., "Sequencing of Pools of Nucleic Acids on Oligonucleotide Arrays," BioSystems 30: 215–31 (1993); WO 92/16655 to Khrapko et al.; Kuznetsova et al., "DNA Sequencing by Hybridization with Oligonucleotides Immobilized in Gel. Chemical Ligation as a Method of Expanding the Prospects for the Method," *Mol. Biol.* 28(20): 290–99(1994); Livits et al., "Dissociation of Duplexes Formed by Hybridization of DNA with Gel-Immobilized Oligonucleotides," *J. Biomolec. Struct. & Dynam.* 11(4): 783–812 (1994), which are hereby incorporated by reference.

WO 89/10977 to Southern, which is hereby incorporated by reference, discloses the use of a support carrying an array of oligonucleotides capable of undergoing a hybridization reaction for use in analyzing a nucleic acid sample for known point mutations, genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

Recently, single strand polymorphism assay ("SSPA") analysis and the closely related heteroduplex analysis methods have come into use as effective methods for screening for single-base mutations (Orita et al., "Detection of Polymorphisms of Human DNA by Gel Electrophoresis as Single-Strand Conformation Polymorphisms," *Proc. Natl. Acad. Sci. USA*, 86:2766–2770 (1989), which is hereby incorporated by reference). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base changes often alter the secondary structure of the molecule sufficiently to cause slight mobility differences between the normal and mutant PCR products after prolonged electrophoresis.

Ligase chain reaction is another method of screening for mutated nucleic acids (see Barany, "Genetic Disease Detection and DNA Amplification Using Cloned Thermostable Ligase," *Proc. Natl. Acad. Sci. USA*, 88:189–193 (1991); Barany, "The Ligase Chain Reaction (LCR) in a PCR World," *PCR Methods and Applications*, 1:5–16 (1991); WO 90/17239 to Barany et al.; Barany et al., "Cloning Overexpression and Nucleotide Sequence of a Thermostable DNA Ligase-Encoding Gene," *Gene*, 109:1–11 (1991); and Barany, "Genetic Disease Detection and DNA Amplification Using Cloned Thermostable Ligase," *Proc. Natl. Acad. Sci. USA* 88:189–193 (1991), which are hereby incorporated by reference). In general, the LCR procedure is carried out with two pairs of oligonucleotide probes: one pair binds to one strand of the target sequence to be detected; the other pair binds to the other complementary strand of the target sequence to be detected. The reaction is carried out by, first, denaturing (e.g., separating) the strands of the target sequence, then reacting the separated strands with the two pairs of oligonucleotide probes in the presence of a heat stable ligase so that each pair of oligonucleotide probes hybridizes to target DNA and, if there is perfect complementarity at their junction, adjacent probes are ligated together. If such complementarity is lacking, no ligation occurs and the probes separate individually from the target sequence during denaturation. The ligated or unligated probes are then separated during the denaturation step. The process is cyclically repeated until the sequence has been amplified to the desired degree. Detection can then be carried out by electrophoresis or by capture hybridization on an array of DNA probes. Ligated and unligated probes can then be detected to identify the presence of a mutation.

The ligase detection reaction (LDR) process is another method for detecting a mutation. It is described generally in WO 90/17239 to Barany et al. Barany et al., "Cloning, Overexpression and Nucleotide Sequence of a Thermostable DNA Ligase-encoding Gene," *Gene,* 109:1–11 (1991), and Barany, "Genetic Disease Detection and DNA Amplification Using Cloned Thermostable Ligase," *Proc. Natl. Acad. Sci. USA,* 88:189–193 (1991), the disclosures of which are hereby incorporated by reference. The ligase detection reaction is similar to the LCR technique; however, in LDR, there is only one pair of oligonucleotide probes which are complementary to one strand of the target sequence. While LCR provides an opportunity for exponential amplification, LDR achieves linear amplification.

Mundy et al. (U.S. Pat. No. 4,656,127, which is hereby incorporated by reference) discusses alternative methods for determining the identity of the nucleotide present at a particular polymorphic site. Mundy's methods employ a specialized exonuclease-resistant nucleotide derivative. A primer complementary to the allelic frequency immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences and unmodified primer and of being extremely sensitive to the rate of polymerase incorporation of the specific exonuclease-resistant nucleotide being used.

Recently, several primer-guided nucleotide incorporation procedures, i.e microsequencing methods, for assaying polymorphic sites (i.e., sites of mutations) in DNA havebeen described (Kornher et al., "Mutation Detection Using Nucleotide Analogs that Alter Electrophoretic Mobility," *Nucl. Acids. Res.,* 17:7779–7784 (1989); Sokolov, "Primer Extension Technique for the Detection of Single Nucleotide in Genomic DNA," *Nucl. Acids Res.,* 18:3671 (1990); Syvanen et al., "A Primer-Guided Nucleotide Incorporation Assay in the Genotyping of Apolipoprotein E," *Genomics,* 8:684–692 (1990); Kuppuswamy et al., "Single Nucleotide Primer Extension to Detect Genetic Diseases: Experimental Application to Hemophilia B (Factor IX) and Cystic Fibrosis Genes," *Proc. Natl. Acad. Sci. USA,* 88:1143–1147 (1991); Prezant et al., "Trapped-Oligonucleotide Nucleotide Incorporation (TONI) Assay, a Simple Method for Screening Point Mutations," *Hum. Mutat.,* 1:159–164 (1992); Ugozzoli et al., "Detection of Specific Alleles by Using Allele-specific Primer Extension Followed by Capture on Solid Support," *GATA,* 9:107–112 (1992); Nyren et al., "Solid Phase DNA Minisequencing by an Enzymatic Luminometric Inorganic Pyrophosphate Detection Assay," *Anal. Biochem.,* 208:171–175 (1993), which are hereby incorporated by reference). These methods differ from Genetic Bit TM Analysis ("GBA TM" discussed extensively below) in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al., "Identification of Individuals by Analysis of Biallelic DNA Markers, Using PCR and Solid-Phase Minisequencing," *Amer. J. Hum. Genet.*, 52:46–59 (1993), which is hereby incorporated by reference).

Cohen et al. (French Patent 2,650,840; PCT Application No. WO 91/02087, which are hereby incorporated by reference) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis TM or GBA TM is described by Goelet et al. (PCT Application No. 92/15712, which is hereby incorporated by reference). In a preferred embodiment, the method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO 91/02087, which are hereby incorporated by reference), the method of Goelet et al. is preferably a heterogeneous phase assay, in which the primer or the target molecule is immobilized to a solid phase. It is thus easier to perform, and more accurate than the method discussed by Cohen.

Other recently developed variations for detecting the presence of mutations include: differential restriction endonuclease digestion (DRED), allele-specific oligonucleotide probing (ASOP)), and ligase-mediated gene detection (LMGD). Additional methods of analysis would also be useful in this context, such as fluorescence resonance energy transfer (FRET) as disclosed by Wolf et al., "Detection of Nucleic Acid Hybridization by Nonradiative Fluorescence Resonance Energy Transfer," *Proc. Nat. Acad. Sci. USA*, 85: 8790–94 (1988), which is hereby incorporated by reference.

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet or red blood cell mRNA is digested and the resulting fragments are analyzed by size. The presence or absence of nucleotide fragments, corresponding to the endonuclease-cleaved fragments, determines which phenotype is present.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a red blood cell or platelet membrane glycoprotein. This specific probe is discernibly labeled so that when it hybridizes to the allele distinguishing cDNA segment, it can be detected, and the specific allele is thus identified.

In the course of the third method of analysis, LMGD, as disclosed by Landegren et al., "A Ligase-Mediated Gene Detection Technique," *Science*, 241: 1077–80 (1988), which is hereby incorporated by reference, a pair of oligonucleotide probes are synthesized that will hybridize adjacently to each other, i.e., to a cDNA segment under appropriate annealing conditions, at the specific nucleotide that distinguishes one allele from other alleles. Each of the pair of specific probes is labeled in a different manner, and when it hybridizes to the allele-distinguishing cDNA segment, both probes can be ligated together by the addition of a ligase. When the ligated probes are isolated from the cDNA segments, both types of labeling can be observed together, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments, both types of labeling are observed separately.

WO 94/11530 to Cantor, which is hereby incorporated by reference, relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin, which is hereby incorporated by reference, uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array.

WO 92/10588 to Fodor et al., which is hereby incorporated by reference, discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et al., U.S. Pat. Nos. 5,143,854 and 5,405,783 to Pirrung et al., WO 90/15070 to Pirrung et al., Pease et al., "Light-generated Oligonucleotide Arrays for Rapid DNA Sequence Analysis", *Proc. Natl. Acad. Sci USA* 91: 5022–26 (1994), which are hereby incorporated by reference. Beattie et al., "Advances in Genosensor Research," *Clin. Chem.* 41(5): 700–09 (1995), which is hereby incorporated by reference, discloses attachment of previously assembled oligonucleotide probes to a solid support.

Landegren et al., "Reading Bits of Genetic Information: Methods for Single-Nucleotide Polymorphism Analysis," *Genome Research,* 8:769–776 (1998), which is hereby incorporated by reference, discloses a review of methods for mutation analysis which are suitable for the present invention.

In another embodiment, testing the biological sample includes amplifying a region of the gene encoding canine RPE65 to provide an amplified fragment before detecting any mutation present in the biological sample.

Amplification of a selected, or target, nucleic acid sequence may be carried out by any suitable means, either to facilitate sequencing or for direct detection of mutations. (See generally Kwoh et al., "Target Amplification Systems in Nucleic Acid-Based Diagnostic Approaches," *Am. Biotechnol. Lab.,* 8:14–25 (1990) which is hereby incorporated by reference.) Examples of suitable amplification techniques include, but are not limited to, polymerase chain reaction, ligase chain reaction ("LCR") strand displacement amplification (see generally, Walker et al., "Strand Displacement Amplification—An Isothermal, In Vitro DNA Amplification Technique," *Nucleic Acids Res.,* 20:1691–1696 (1992); Walker et al., "Isothermal In-Vitro Amplification of DNA By a Restriction Enzyme-DNA Polymerase System," *Proc. Natl. Acad. Sci. USA* 89:392–396 (1992), which are hereby incorporated by reference), transcription-based amplification (see Kwoh et al., "Transcription-Based Amplification System and Detection of Amplified Human Immunodeficiency Virus Type 1 With a Bead-Based Sandwich Hybridization Format," *Proc. Natl. Acad. Sci. USA* 86:1173–1177 (1989), which is hereby incorporated by reference), self-sustained sequence replication (or "3SR") (see Guatelli et al., "Isothermal In-Vitro Amplification of Nucleic Acids By a Multienzyme Reaction Modeled After Retroviral Replication," *Proc. Natl. Acad. Sci. USA* 87:1874–1878 (1990), which is hereby incorporated by reference), the Qβ replicase system (see Lizardi et al., "Exponential Amplification of Recombinant RNA Hybridization Probes," *Biotechnology,* 6:1197–1202 (1988), which is hereby incorporated by reference), nucleic acid sequence-based amplification (or "NASBA") (see Lewis, "Review of Progress in Developing Amplification Technologies Which May Compete With Roche Diagnostic Systems' Polymerase Chain Reaction (PCR)," *Genetic Engineering News,* 12(9):1, 8–9 (1992), which is hereby incorporated by reference), the repair chain reaction (or "RCR") (see Lewis, "Review of Progress in Developing Amplification Technologies Which May Compete With Roche Diagnostic Systems' Polymerase Chain Reaction (PCR)," *Genetic Engineering News,* 12(9) :1, 8–9 (1992), which is hereby incorporated by reference), and boomerang DNA amplification (or "BDA") (see Lewis, "Review of Progress in Developing Amplification Technologies Which May Compete With Roche Diagnostic Systems' Polymerase Chain Reaction (PCR)," *Genetic Engineering News,* 12(9):1, 8–9 (1992), which is hereby incorporated by reference). Polymerase chain reaction is currently preferred.

Genomic sequence-specific amplification technologies, such as the polymerase chain reaction (Mullis et al., "Specific Enzymatic Amplification of DNA in-Vitro the Polymerase Chain Reaction," *Cold Spring Harbor Symp. Quant. Biol.* 51:263–274 (1986); European Patent Application No. 50,424 to Erlich et at.; European Patent Application No. 84,796 to Erlich et al.; European Patent Application 258,017 to Erlich et al.; European Patent Application No. 237,362 to Erlich et al.; European Patent Application No. 201,184 to Mullis; U.S. Pat. No. 4,683,202 to Mullis et al.; U.S. Pat. No. 4,582,788 to Erlich; Saiki et al., "Enzymatic Amplification of Beta Globin Genomic Sequences and Restriction Site Analysis for Diagnosis of Sickle Cell Anemia," *Science* 230:1350–1354 (1985); and U.S. Pat. No. 4,683,194 to Saiki et al., which are hereby incorporated by reference), may be employed to facilitate the recovery of the desired polynucleotides. In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

In a preferred embodiment, testing the biological sample includes performing PCR using genomic DNA templates and polyacrylamide gel electrophoresis (PAGE). In particular, PCR is performed using primers spanning the location of the mutation. The sizes of the amplified DNA fragments from homozygous normal and affected dogs are different. Subsequently, the amplified DNA fragments are electrophoresed using PAGE.

In one embodiment of the invention, the testing of the genetic material in the biological sample is carried out by Taq cycle sequencing. The method for cycle sequencing, based on linear amplification of template DNA by polymerase chain reaction, was described by Murray, "Improved Double Stranded Sequencing Using the Linear Polymerase Chain Reaction," *Nucleic Acids Research,* 17:88–89 (1989), which is hereby incorporated by reference. This technique essentially combines thermocycling procedure using Taq polymerase with dideoxy sequencing. In principle, the sequencing reaction consists of primer annealing to the template DNA followed by repeated extension of the primer by Taq polymerase in the presence of dNTPs/ddNTPs, linearly amplifying the sequence reaction products. Currently, cycle sequencing is done almost exclusively by non-isotopic methods using an automated DNA sequencer. A popular format for the sequencing protocol developed by Probe et al., "A System for Rapid DNA Sequencing with Fluorescent Chain-Terminating Dideoxynucleotides," *Science,* 238:336–341 (1987), which is hereby incorporated by reference, is based on the use of a set of four chain-terminating dideoxynucelotides, each coupled to a different fluorescent dye and distinguishable by fluorescence emission. The DNA fragments arc resolved by gel electrophoresis in one sequencing lane and detected by a scanning fluorescence detection system with computer-based automatic sequence identification.

One method that can be used to detect a mutation is polymerase chain reaction restriction fragment length polymorphism (PCR-RFLP). Single nucleotide changes in the genes are common phenomenon. Such alterations, depending on their locations, can be innocuous or deleterious to the gene function. Single base changes can alter the recognition sequence of restriction enzymes resulting in creation of a new, or abolition of an existing, restriction site, giving rise to variation in DNA fragment length. The variants are called restriction fragment length polymorphism (RFLP). These are inherited in a codominant fashion and are allelic variants, generating homozygous and heterozygous genotypes. Identification of RFLP in mammalian genome has been classically determined by Southern blot analysis. Use of polymerase chain reaction (PCR) to detect RFLP has dramatically accelerated the pace of initial identification and subsequent assaying of a large number of samples in an easy to use format. In short, two oligonucleotide primers are designed from the region of the genome flanking the suspected variation in the sequence between two alleles. These primer pairs are used to amplify the encompassing region of interest from genomic DNA by PCR using Taq polymerase and dNTPs in the presence of an optimal concentration of magnesium chloride. The PCR products are digested with the restriction enzyme with altered recognition sites between two alleles of the genome, and the digested DNA fragments are separated by electrophoresis in a solid matrix of choice (e.g., agarose or polyacrylamide) depending on the size of the fragments. (See, e.g., Ray et al., "Molecular Diagnostic Test for Ascertainment of Genotype at the Rod Cone Dysplasia (rcd1) Locus in Irish Setters," *Current Eye Research*, 14:243–247 (1995); Ray et al., "A Highly Polymorphic RFLP Marker in the Canine Transducin α-1 Subunit Gene," *Animal Genetics*, 27:372–373 (1996); Ray et al., "PCR/RFLP Marker in the Canine Opsin Gene," *Animal Genetics*, 27:293–294 (1996); Wang et al., "PCR/RFLP Marker in the Canine Transducin-γ Gene (GNGT1)," *Animal Genetics*, 28:319–320 (1997); Gu et al., "Detection of Single Nucleotide Polymorphism," *BioTechniques*, 24:836–837 (1998) and Zeiss et al., "A Highly Polymorphic RFLP Marker in the Canine Retinitis Pigmentosa GTPase Regulator (RPGR) Gene," *Animal Genetics*, 29:409 (1998), which are hereby incorporated by reference). In addition to the rapidity of the PCR-RFLP technique, it also offers the flexibility to create an allele specific restriction site when the nucleotide change does not naturally create a RFLP. This is routinely done by deliberately incorporating a mismatch nucleotide in one of the primers such that a restriction site is created in one of the two alleles.

Nickerson et al. have described a nucleic acid detection assay that combines attributes of PCR and OLA (Nickerson et al., "Automated DNA Diagnostics Using an Elisa-Based Oligonucleotide Ligation Assay," *Proc. Natl. Acad. Sci. USA*, 87:8923–8927 (1990), which is hereby incorporated by reference). In this method, PCR is used to achieve the exponential amplification of target DNA, which is then detected using OLA.

Another aspect of the present invention is a method for selecting dogs for breeding which includes obtaining a biological sample from a dog, testing the biological sample for a gene encoding canine RPE65 having a nucleic acid mutation in one or both alleles indicative of a carrier of or a dog affected with congenital stationary night blindness, and eliminating dogs with the mutation from a breeding stock or breeding the dogs with the mutation with genetically normal dogs. This method allows affected or carrier dogs to be eliminated from the breeding stock or bred to genetically normal dogs which do not have a nucleic acid mutation in a gene encoding RPE65.

Yet another aspect of the present invention is an isolated nucleic acid molecule including a DNA molecule having the nucleotide sequence selected from the group consisting of SEQ. ID. No. 4, SEQ. ID. No. 5, SEQ. ID. No. 6, SEQ. ID. No. 7, and SEQ. ID. No. 8. These isolated nucleic acid molecules can be used as a forward primer, a reverse primer, a vector specific reverse primer, a vector specific forward primer, and a consensus primer, respectively, to amplify canine RPE65 cDNA.

EXAMPLES

Example 1

Animals

Briard dogs affected with csnb and related and unrelated phenotypically normal dogs were examined to characterize the disease phenotype, and examine for mutations in the RPE65 gene. Overall, 15 briard dogs were studied, of which 10 were affected with csnb, and 5 were clinically normal. These dogs came, primarily, from the United States and Canada of breeding stock that originated from the United States and France. In addition, samples were tested from 4 Swedish dogs, both purebred briard or briard-beagle crosses, of which 2 were affected and 2 heterozygous for the reported 4 nucleotide deletion in the RPE65 gene. Lastly, samples were tested from 4 littermate briard dogs which had previously been examined. One individual from this last group of 4 dogs was clinically affected with a retinal degenerative disorder. This dog, at 6 years of age, showed evidence of night blindness, hesitant behavior in bright light, and ophthalmoscopically visible retinal thinning and vascular attenuation characteristic of mid-stage progressive retinal atrophy (PRA; Parshall et al., "Photoreceptor Dysplasia: An Inherited Progressive Retinal Atrophy Of Miniature Schnauzer Dogs," *Prog. Vet. Comp. Ophthalm.*, 1:187–203 (1991), which is hereby incorporated by reference). ERG testing confirmed the retinal disorder, and indicated that only cone mediated responses were recordable.

All dogs studied were subjected to a comprehensive clinical ophthalmic examination, including indirect ophthalmoscopy and slit lamp biomicroscopy. In addition, a selected number of dogs underwent ERG testing as previously described (Aguirre et al., "Variation In Retinal Degeneration Phenotype Inherited At the Prcd Locus," *Exp. Eye Res.*, 46:663–687 (1988), which is hereby incorporated by reference). Briefly, the ERG was recorded from the halothane anesthetized dog using a stimulus protocol which, by differentially eliciting rod and cone components of the ERG, allows their separate evaluation (Parshall et al., "Photoreceptor Dysplasia: An Inherited Progressive Retinal Atrophy Of Miniature Schnauzer Dogs," *Prog. Vet. Comp. Ophthalm.*, 1:187–203 (1991); Aguirre et al., "Variation In Retinal Degeneration Phenotype Inherited At The Prcd Locus," *Exp. Eye Res.*, 46:663–687 (1988); Aguirre, "Rod And Cone Contributions To The Canine Electroretinogram," Ph.D. Thesis. University of Pennsylvania, 1975; Acland et al., "Retinal Degenerations In The Dog: IV. Early Retinal Degeneration (Erd) In Norwegian Elkhounds," *Exp. Eye Res.*, 44:491–521 (1987), which are hereby incorporated by reference). Signal averaging of very low amplitude responses also was carried out to examine the waveform of these responses.

The eyes from 2 dogs, 4.3 and 10.7 months of age, were removed following euthanasia by barbiturate overdose, and the eyes processed for microscopic examination using methods previously described for embedding either in plastic (4.3 months, both eyes) (Acland et al., "Retinal Degenerations In The Dog: IV. Early Retinal Degeneration (Erd) In Norwegian Elkhounds," *Exp. Eye Res.*, 44:491–521 (1987), which is hereby incorporated by reference) or in the synthetic wax diethylene glycol distearate (DGD; 10.7 months, one eye) (Huang et al., "Diethylene Glycol Distearate (DGD): A Versatile Embedding Medium For Retinal Cytochemistry," *J. Neurosci. Methods*, 47:227–234 (1993), which is hereby incorporated by reference). The tissues were sectioned at 1 μm and stained with azure II/methylene blue. The retina of the fellow eye of the 10.7 month old dog was isolated under sterile conditions, and kept frozen at −70° C. until used for these studies. All procedures involving animals were undertaken in strict compliance with the guidelines of the U.S. Public Health Service's policy on the Humane Care and Use of Laboratory Animals, and the ARVO Resolution on the Use of Animals in Ophthalmic and Vision Research.

Example 2

Genomic DNA and RNA Samples

Genomic DNA was isolated using standard techniques (Sambrook et al., "Molecular Cloning: A Laboratory Manual," Cold Spring Harbor Laboratory, Cold Spring Harbor, N.Y. (1989), which is hereby incorporated by reference) from either blood samples collected in citrate anticoagulant tubes, or from splenic samples from deceased dogs. Retina from the enucleated fellow eye of the 10.7 month old affected dog was utilized for RNA extraction; total RNA was isolated from retina using the guanidium-phenol procedure previously described (Chomzynski et al., "Single-Step Method For RNA Isolation By Acid-Guanidium Thiocyanate Phenol-Chloroform Extraction," Anal. Biochem., 172:156–159 (1987), which is hereby incorporated by reference).

Example 3

Reverse Transcription (RT) and Polymerase Chain Reaction (PCR)

Screening of a Canine Retinal cDNA Library for RPE65 Clone by PCR

The canine retinal cDNA library was custom made (Stratagene Cloning Systems, La Jolla, Calif.) from poly-A$^+$ RNA isolated from retinas of homozygous normal miniature poodles. RPE65 cDNA sequence was retrieved from the cDNA library by polymerase chain reaction (PCR) based screening of the library. A forward primer (RPE65-1; 5'-CAA TGC CCT TGT TAA TGT CTA CCC AG-3')) (SEQ. ID. No. 4) and a reverse primer (RPE65-3; 5'-CCT GCT TAA TTG TCT CCA AGG TCT C-3') (SEQ. ID. No. 5) were designed from the consensus region of human (GenBank Accession No. U18991), bovine (GenBank Accession Nos. L11356, and X66277), and rat (GenBank Accession No. AF035673) RPE65 cDNA sequences. The gene specific forward primer, RPE65-1, was used in combination with a vector specific reverse primer (pBK-V; 5'-CCG CTC TAG AAG TAC TCT CGA GTT-3') (SEQ. ID. No. 6) to amplify the 3'-region of the canine homologue of RPE65 cDNA. Similarly, the gene specific reverse primer, RPE65-3, was used in combination with the vector specific forward primer (pBK-III; 5'-GGT CGA CAC TAG TGG ATC CAA AG-3') (SEQ. ID. No. 7) to amplify the 5'-region of the canine RPE65 cDNA which would have a overlapping region with the amplified 3' cDNA fragment. PCR was done for 30 cycles (94° C. for 1 minute, 60° C. for 1 minute, 72° C. for 2 minutes, with a final extension at 72° C. for 10 minutes) using 0.4 μM of each primer pair in a volume of 50 μl containing 50 mM KCl, 10 mM Tris-HCl (pH 8.3), 2 mM MgCl$_2$, and 0.2 mM each dATP, dCTP, dGTP, and dTTP.

RT-PCR from Canine Retina

A 540 nucleotide long 5'-region of canine RPE65 cDNA was successfully amplified by PCR from the retinal cDNA library, but the 3'-region of the cDNA did not yield PCR product containing the remainder of the coding sequence. To clone the 3' end, a new consensus primer (RPE65-8; 5'-TGC TTG CTC AAC TCA GTG CTT TCT G-3') (SEQ. ID. No. 8) was designed, as described above, from the 3'-untranslated region (UTR) of mammalian RPE65. A 1400 bp DNA fragment was amplified by RT-PCR using the RPE65-1 and RPE65-8 primer pair from total RNA isolated from retina using RNA PCR kit (Perkin Elmer, Foster City, Calif.). The identity of the amplified DNA fragment was confirmed to be RPE65 by direct sequencing of the PCR product, and comparison with previously published homologous sequences using the BLAST service. PCR conditions were as above.

PCR Using Genomic DNA Templates

To identify, the presence of a mutation in the canine RPE65 gene and examine for cosegregation of the mutation and the disease, PCR was undertaken for 30 cycles (94° C. for 30 seconds, 60° C. for 1 minute, 72° C. for 1 minute, with a final extension at 72° C. for 5 minutes) using primers RPE65-1 (SEQ. ID. No. 4) and RPE65-3 (SEQ. ID. No. 5) selected from a single exon (putative exon 5) spanning the location of the mutation. The sizes of the DNA fragments amplified from homozygous normal and csnb-affected dogs were 109 bp and 105 bp, respectively. The amplified DNA fragments were electrophoresed in a 6% non denaturing polyacrylamide gel using TBE buffer (0.089M Tris-borate and 0.002M EDTA, pH 8).

Example 4

DNA Sequencing

PCR amplified DNA fragments were used directly for sequencing after purification of the samples. Sequencing was accomplished by Taq cycle sequencing using Dye Deoxy terminators in an Applied Biosystems automated sequencer (ABI 377 DNA sequencer, ABI Applied Biosystems, Inc., Foster City, Calif.). Sequence manipulation and comparison were undertaken using programs Seqed (ABI Applied Biosystems, Inc., Foster City, Calif.) and Gene Jockey II (Biosoft, Cambridge, UK), and the Genbank BLAST service (Altschul et al., "Basic Local Alignment Search Tool," J. Mol. Biol., 215:403–410 (1990), which is hereby incorporated by reference).

Example 5

Clinical and Morphologic Characterization of csnb 10 briard dogs affected with csnb that originated from stock in the United States, Canada, and France were examined; in addition, 5 clinically non-affected briards which were related to the affected dogs in this study were examined. The obligate heterozygous animals had normal ophthalmic examination; prior studies have shown that visual function and the ERG of heterozygous animals is normal. In contrast, the affected dogs had a severe impairment of visual function which primarily affected night vision, but, in some cases, day vision was affected to various degrees. When young, some of the animals had distinct nystagmus which disappeared with aging, but could be induced with excitement; no other abnormalities were recognized on clinical ophthalmic exam. The one older affected dog that was available for examination at 4 years of age also showed no abnormalities on ophthalmologic examination.

Electroretinography of affected dogs showed that the rod and cone mediated responses were severely depressed in amplitude in comparison to those recorded from normal dogs (FIG. 2). In general, the responses appeared diminutive or non-recordable under most recording conditions, especially when the retina was stimulated with weak illumination. Higher intensity flickering light stimuli which elicited cone-mediated responses often resulted in low amplitude signals. Signal averaging showed the presence of small amplitude responses which often had a normal waveform, similar to a "Riggs type" ERG in man (Narfström et al., "The Briard Dog: A New Animal Model Of Congenital Stationary Night Blindness," Br. J. Ophthalmol., 73:750–756 (1989), which is hereby incorporated by reference).

Figure 3:
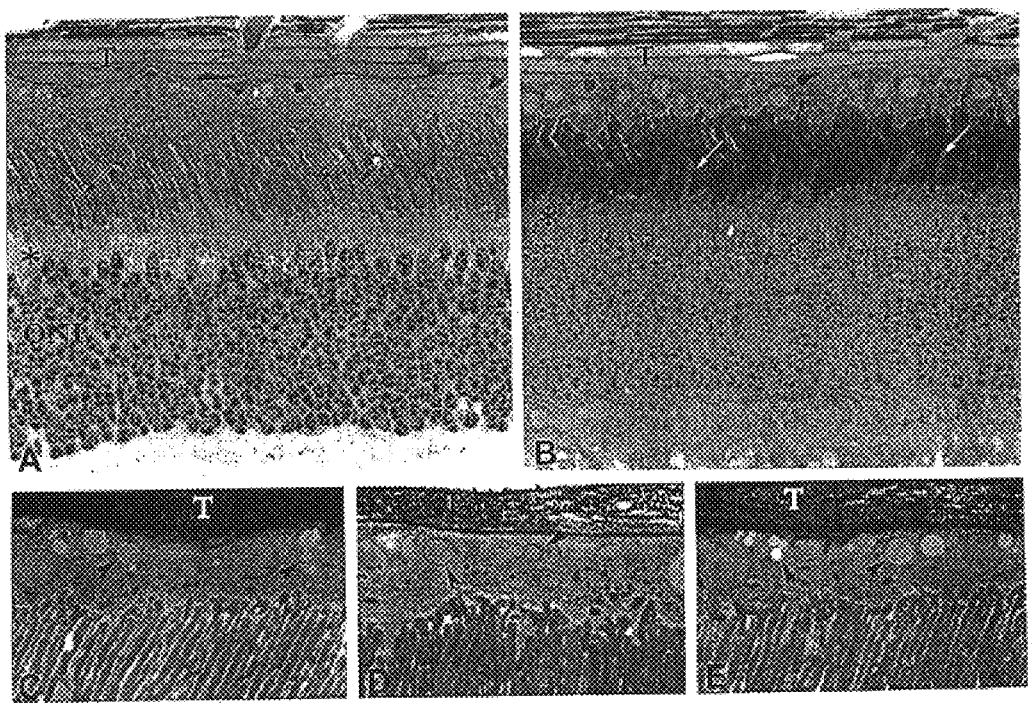
FIGS. 3A–E show histologic sections of plastic embedded retina from a 4.3 month old dog affected with congenital stationary night blindness. Sections are taken from the tapetal zone (T) in the superior quadrant, near the posterior pole (A) or the midperiphery (B). The retina is of normal thickness, and there is a normal number of photoreceptor cells and nuclei in the outer nuclear layer (ONL). The rod outer segments appear slightly irregular, particularly in the posterior pole (A), but are structurally better preserved in the mid-periphery (B). The variable shortening of rod inner segments results in outer segments of differing lengths. Cone inner segments appear elongated and distinct (FIGS. 3A, 3B-oblique arrows). Cytoplasmic inclusions are present in the retinal pigment epithelium ("RPE") (FIGS. 3C–E, arrowheads). These occur as single small inclusions, or form aggregates or larger inclusions which can be homogeneous or vacuolated. * external limiting membrane.

Light microscopic examination of the retinas showed pathologic changes limited to the retinal pigment epithelium (RPE) and photoreceptor layers. These abnormalities were most distinct in plastic embedded sections of the retina of the younger dog (4.3 months), but were also evident in the eye from the older affected dog that was embedded in DGD. The photoreceptor outer segments appeared normal, particularly in the periphery, but showed slight disorganization in the posterior pole and equator (FIG. 3A). Additionally, there was an uneven shortening of the rod inner segments which caused the rod outer segments to have a variable length, even when structurally normal (FIG. 3B). The shortening of the rod inner segments resulted in increased prominence of the cones in the photoreceptor layer. The most remarkable abnormalities, however, were present in the RPE, and consisted of the accumulation of cytoplasmic inclusions of variable size. These inclusions were single to multiple, and were vacuolated or appeared homogeneous (FIG. 3C–E). The RPE inclusions appeared to coalesce and were much larger in the 10.7 month old dog. The RPE appeared somewhat reactive in that the cells were slightly hypertrophied, and their apical surfaces were irregular. At the two ages examined, there were no other pathologic changes in the retina, and no evidence of photoreceptor degeneration or cell death as indicated by the presence of an outer nuclear layer of normal thickness.

Example 6

Characterization of the Canine RPE65 cDNA

Overlapping fragments of normal canine RPE65 cDNA were amplified from the retinal cDNA library by PCR, and from retinal RNA by RT-PCR. The characterized region of normal canine RPE65 cDNA spans 1724 nucleotides (GenBank Accession No. AF084537), and includes 1602 nucleotides of coding sequence predicted to encode a protein of 533 amino acids (61 kDa), 27 nucleotides of 5'-UTR, and 94 nucleotides of 3'-UTR (FIG. 1). Over the coding region, the canine RPE65 gene shares 88%–89% nucleotide sequence identity with homologous human and bovine sequences, and 83% identity with rat sequence. The deduced amino acid sequence shares 98, 97, and 93% identity with homologous human, bovine, and rat sequences, respectively.

Example 7 csnb Results from the Same Mutation in the RPE65 Gene Causing Retinal Dystrophy in Swedish Briard Dogs Once the normal canine RPE65 cDNA was characterized, the cDNA was amplified from csnb affected retinal RNA and compared with the normal. It was observed that the four nucleotide (AAGA) deletion reported to cause retinal dystrophy in Swedish briards is present in csnb affected briards in the USA and Canada (Gal et al., "Mutation Spectrum Of RPE65 In Autosomal Recessive Childhood-Onset Severe Retinal Dystrophy," *Supp. Inv. Ophthalm. Vis. Sci.*, 39:S901 (1998), which is hereby incorporated by reference). The deleted nucleotides (AAGA) represent nucleotides 487–490 of wildtype canine RPE65 sequence, and correspond to nucleotides 340–343 of human exon 5 (Genbank Accession No. U20479). The mutation produces a frameshift, causing a deduced mistranslation of (now) nucleotides 487 through 645, with a stop at (now) codon 205 (nucleotides 643–645 of mutant sequence). No other disease causing mutations were identified in the sequence obtained from the affected dogs.

Figure 4:
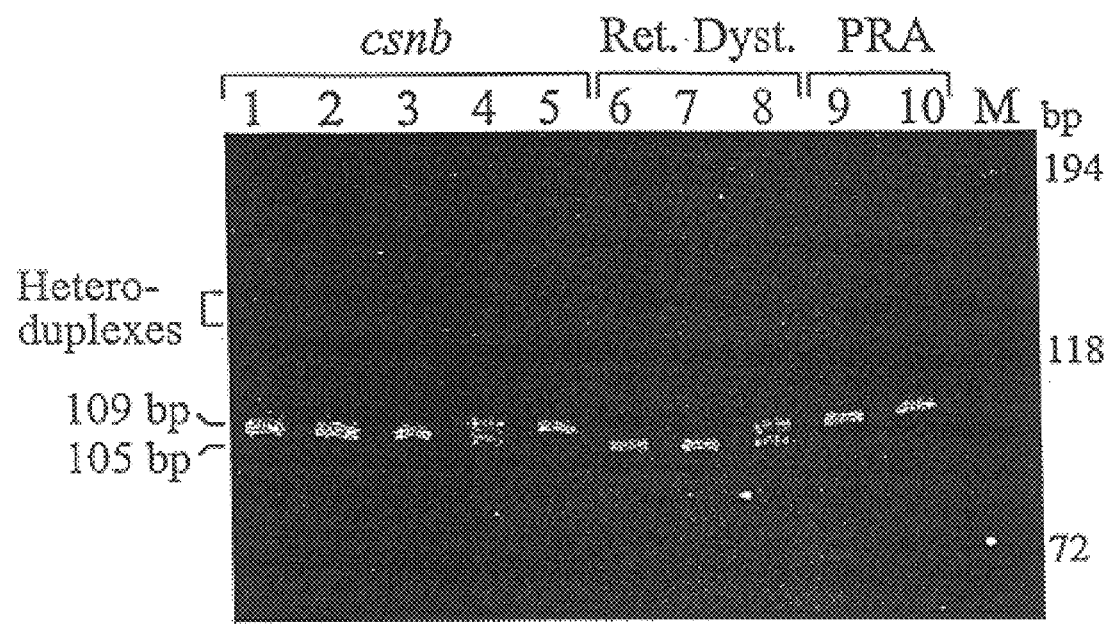
FIG. 4 shows the amplification of putative exon 5 of RPE65 gene from briard dogs affected with csnb, retinal dystrophy (Ret. Dyst.) and progressive retinal atrophy ("PRA"). A small region of exon 5 was amplified by PCR from (a) csnb affected (lanes 1–3), carrier (lane 4), and normal (lane 5) dogs of United States and Canadian origin; (b) Swedish briard dogs affected with retinal dystrophy (lanes 6 and 7) or carrier for the disease (lane 8); and (c) PRA affected (lane 9) and nonaffected littermate (lane 10) briard dogs of United States origin. The PCR products were separated in 6% non denaturing polyacrylamide gel. The sizes of the amplified DNA fragments from the two alleles, and the relative location of the heteroduplexes formed between these two alleles in the gel are indicated. The marker lane (M) contains 100 bp DNA ladder.

To identify the mutation from genomic DNA in suspected dogs, a region of putative exon 5 encompassing the site of the mutation was amplified. As shown in FIG. 4, PCR using genomic DNA from csnb affected and normal briard dogs resulted in amplification of DNA fragments 105 bp and 109 bp long, respectively. As expected, PCR product from an obligate heterozygote dog contained both the alleles. Also, the presence of two distinct heteroduplex bands with slower mobility in the polyacrylamide gel is a typical observation associated with PCR products of heterozygous samples containing two alleles resulting from a short insertion or deletion. To determine if the mutation identified in csnb-affected dogs was the same as the one described for Swedish dogs with retinal dystrophy, 2 affected and 2 heterozygous dogs were analyzed, and the results were identical to the observation made for csnb alleles in the United States and Canadian briard dogs (FIG. 4). Sequencing of the amplified DNA fragments from the normal and csnb affected briard revealed deletion of four nucleotides (AAGA).

Example 8

Cosegregation of the RPE65 Mutation in csnb Affected Briard Pedigree

Figure 5:
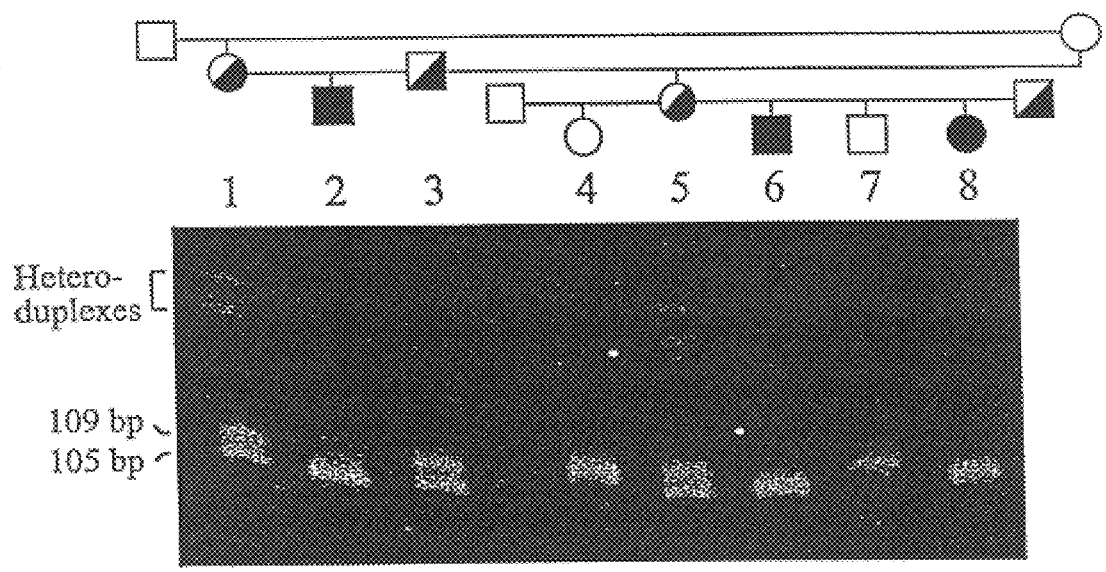
FIG. 5 shows the mendelian inheritance of the RPE65 mutation in a briard pedigree informative for csnb. Affected dogs are represented by black squares (males) and circles (females); obligate heterozygous and clinically non-affected dogs are represented by half filled and open symbols, respectively. The region of RPE65 exon 5 containing the mutation was amplified from genomic DNA of individual dogs, and the PCR products were separated in a 6% non denaturing polyacrylamide gel. Each lane in the illustration shows PCR product obtained from DNA samples of the dog corresponding to the lane. Some of the dogs of the pedigree from which the DNA samples were not available do not correspond to any marked lane of the gel. PCR products from the affected dogs (lanes 2, 6, and 8) contain only the smaller DNA fragment (105 bp) due to the presence of a 4 nucleotide deletion. Homozygous normal dogs (lanes 4 and 7) contain the normal allele, hence the larger DNA fragment (109 bp). As expected, PCR products from the obligate heterozygotes (lanes 1, 3, and 5) contain both of the DNA fragments, and the heteroduplexes formed between the complementary strands of the 2 alleles.

Once the 4 nucleotide deletion in the RPE65 gene was identified in csnb affected dogs, a briard pedigree informative for csnb was examined to determine if the mutation cosegregated with the disease. In the animals available for molecular testing, complete cosegregation of the mutation with the disease was found; affected dogs were homozygous for the 4 nucleotide deletion while obligate carriers were heterozygous for the normal and mutant alleles. In this small pedigree, it was possible to readily differentiate the homozygous normal from heterozygous samples from phenotypically normal animals which were either genetically normal or carriers (FIG. 5).

Example 9

Progressive Retinal Atrophy (PRA) in the Briard Dogs is Not Associated with the RPE65 Mutation Causing csnb and Retinal Dystrophy To determine if this mutation in the RPE65 gene was associated with PRA in the briard, samples from 4 littermate dogs of this breed in which a diagnosis of PRA had been made in one of them were tested on the basis of the characteristic visual, ophthalmoscopic, and ERG abnormalities. No abnormality was found in the region of the RPE65 gene which harbors the mutation responsible for csnb, either in the PRA-affected dog or in its normal littermates (FIG. 4, right panel).

Example 10

Identification of csnb in Dogs

The clinical, electrophysiologic, and pathologic features of retinal dystrophy in the briard dog have been reported in a series of very detailed studies from Sweden (Narfström et al., "Hereditary Retinal Dystrophy In The Briard Dog: Clinical And Hereditary Characteristics," *Veterinary & Comparative Ophthalmology*, 4:85–92 (1994); Narfström et al., "The Briard Dog: A New Animal Model Of Congenital Stationary Night Blindness," *Br. J. Ophthalmol.*, 73:750–756 (1989); Wrigstad et al., "Slowly Progressive Changes Of The Retina And Retinal Pigments Epithelium In Briard Dogs With Hereditary Retinal Dystrophy. A Morphologic Study," *Doc. Ophthalmol.*, 87:337–354 (1994); Wrigstad, "Hereditary Dystrophy Of The Retina And The Retinal Pigment Epithelium In A Strain Of Briard Dogs: A Clinical, Morphologic And Electroretinographic Study," Linköping University Medical Dissertation #423 (1994); Nilsson et al., "Changes In The DC Electroretinogram In Briard Dogs With Hereditary Congenital Night Blindness And Partial Day Blindness," *Exp. Eye Res.*, 54:291–296 (1992), which are hereby incorporated by reference). The disease has a characteristic clinical phenotype, consisting of profound visual impairment present soon after the dog is sufficiently mature to test visual function (5–6 weeks of age), and a normal appearing fundus, at least for the first 3–4 years of age. Older dogs may show subtle retinal abnormalities indicative of a slowly progressive retinal degenerative process. The ERG responses, both rod and cone mediated, are also abnormal, and the DC ERG suggests a defect in the phototransduction process (Nilsson et al., "Changes In The DC Electroretinogram In Briard Dogs With Hereditary Congenital Night Blindness And Partial Day Blindness," *Exp. Eye Res.,* 54:291–296 (1992), which is hereby incorporated by reference). Surprisingly, the photoreceptor cells do not show extensive pathologic abnormalities, at least in the early stages of the disease, that would be expected for animals with such functional deficits. The RPE has shown a dramatic accumulation of lipoidal inclusions (Wrigstad et al., "Slowly Progressive Changes Of The Retina And Retinal Pigments Epithelium In Briard Dogs With Hereditary Retinal Dystrophy. A Morphologic Study," *Doc. Ophthalmol.,* 87:337–354 (1994); Wrigstad et al., "Ultrastructural Changes Of The Retina And The Retinal Pigment Epithelium In Briard Dogs With Hereditary Congenital Night Blindness And Partial Day Blindness," *Exp. Eye Res.,* 55:805–818 (1992), which are hereby incorporated by reference) which, until now, appeared to be an unexplained byproduct of the disease process (see below).

Because of the clinical similarities in phenotype between retinal dystrophy and csnb, a disease identified in briard dogs from the United States and Canada, a selected population of briards was examined using methods which would evaluate the clinical, functional, and morphologic characteristics of csnb in a manner that was analogous to the studies done on the Swedish dogs. With the limitation imposed by using slightly different methods, the results are totally compatible to those published by Narfström and associates in their studies (Narfström et al., "Hereditary Retinal Dystrophy In The Briard Dog: Clinical And Hereditary Characteristics." *Veterinary & Comparative Ophthalmology,* 4:85–92 (1994); Narfström et al., "The Briard Dog: A New Animal Model Of Congenital Stationary Night Blindness," *Br. J. Ophthalmol.,* 73:750–756 (1989), Wrigstad, "Hereditary Dystrophy Of The Retina And The Retinal Pigment Epithelium In A Strain Of Briard Dogs: A Clinical, Morphologic And Electroretinographic Study," Linköping University Medical Dissertation #423 (1994), which are hereby incorporated by reference). At least on a clinical and morphologic basis, it can be concluded that csnb and retinal dystrophy appear to represent the same disorder. Based on the 4 nucleotide deletion in the RPE65 gene that was reported to be causally associated with retinal dystrophy in briards (Gal et al., "Mutation Spectrum Of RPE65 In Autosomal Recessive Childhood-Onset Severe Retinal Dystrophy," *Supp. Inv. Ophthalm. Vis. Sci.,* 39:S901 (1998), which is hereby incorporated by reference), the canine RPE65 cDNA was cloned and characterized to determine if a mutation in this gene was present in csnb, and if it was the same as that causing retinal dystrophy in the Swedish dogs.

Previous reports have indicated that the RPE65 gene is exclusively expressed in the RPE (Hamel et al., "Molecular Cloning And Expression Of RPE65, A Novel Retinal Pigment Epithelium-Specific Microsomal Protein That Is Post-Transcriptionally Regulated In Vitro," *J. Biol. Chem.,* 268:15751–15757 (1993); Nicoletti et al., "Molecular Characterization Of The Human Gene Encoding An Abundant 61 kDa Protein Specific To The Retinal Pigment Epithelium," *Hum. Mol. Genet.,* 4:641–649 (1995), which are hereby incorporated by reference). However, the cDNA from a retinal cDNA library was characterized on the premise that even a low level of expression of the gene in the tissue would be sufficient for amplification of the coding sequence, and characterization of the UTR. The characterized region of normal canine RPE65 cDNA spans 1724 nucleotides (GenBank Accession No. AF084537), and includes 1602 nucleotides of coding sequence predicted to encode a protein of 533 amino acids (61 kDa), 27 nucleotides of 5'-UTR and 94 nucleotides of 3'-UTR. Comparison of the sequence between the normal and csnb-affected dog indicated that in the affected dog there was a 4 nucleotide deletion (AAGA) in the putative exon 5 of the RPE65 gene which was the same as described by Gal and associates for dogs with retinal dystrophy. The deleted nucleotides (AAGA), represent nucleotides 487–490 of wildtype canine RPE65 sequence, and correspond to nucleotides 340–343 of human exon 5. The mutation produces a frameshift, causing a deduced mistranslation with a stop at (now) codon 205 (nucleotides 643–645 of the mutant sequence), and a presumably non-functional RPE65 gene product.

To establish if the observed mutation was causally associated with the disease, a region of the putative exon 5 encompassing the site of the mutation was amplified from genomic DNA. In a 3 generation pedigree informative for csnb, the cosegregation of the mutant allele with 100% concordance could be established. These dogs were part of a larger sample of 15 briard dogs whose disease status was known, and derived from breeding stock that originated from the United States and France. In all cases, affected dogs showed the homozygous 4 nucleotide deletion of the RPE65 gene, while obligate heterozygous dogs had the mutation in only one allele. Lastly, 4 Swedish briard or briard-beagle crosses, 2 affected and 2 heterozygous were tested for retinal dystrophy (Narfström et al., "Hereditary Retinal Dystrophy In The Briard Dog: Clinical And Hereditary Characteristics," *Veterinary & Comparative Ophthalmology,* 4:85–92 (1994), which is hereby incorporated by reference), and the same mutation was found. Identification of same mutation in briards with csnb and retinal dystrophy confirmed the molecular identity of the 2 disorders. Furthermore, because some of the dogs tested in this study were apparently unrelated, the finding of a common mutation in dogs derived from different countries suggests a founder effect causing the propagation of a common mutant allele in the population at risk.

Progressive retinal atrophy ("PRA") is also present sporadically in the briard breed, and the clinical and functional abnormalities identified in the intermediate stages of the disease could be compatible with those present in older dogs affected with csnb. To exclude the 4 nucleotide deletion in the RPE65 gene from causal association with PRA, samples from 4 littermate briard dogs were tested, 1 PRA affected and 3 non-affected. For the region of the RPE65 gene examined by PCR, the 4 nucleotide deletion that results in csnb was not found. Thus, this mutation could be excluded as a cause of PRA in this dog breed.

In their 1997 paper, Gu and associates described 5 different mutations in the RPE65 gene responsible for autosomal recessive childhood-onset severe retinal dystrophy (Gu et al., "Mutations In RPE65 Cause Autosomal Recessive Childhood-Onset Severe Retinal Dystrophy," *Nat. Genet.,* 17:194–197 (1997), which is hereby incorporated by reference). Most patients had severe visual deficits present at birth or within the first decade of life. Ophthalmoscopic abnormalities varied from vascular attenuation and optic disc atrophy without bone spicules to lesions typical of advanced Retinitis Pigmentosa ("RP") in adults. In these patients, the disease progresses to severe visual impairment and blindness, and concomitant ophthalmoscopic abnormalities indicative of advanced retinal degeneration (Gu et al., "Mutations In RPE65 Cause Autosomal Recessive Childhood-Onset Severe Retinal Dystrophy," *Nat. Genet.*, 17:194–197 (1997), which is hereby incorporated by reference). Similar abnormalities have been described in a second study of the disease (Marlhens et al., "Mutations In RPE65 Cause Leber's Congenital Amaurosis," *Nat. Genet.*, 17:139–141 (1997), which is hereby incorporated by reference). More recently, mutations in this gene have been causally associated with autosomal recessive RP or Leber congenital amaurosis (Morimura et al., "Mutations In The RPE65 Gene In Patients With Autosomal Recessive Retinitis Pigmentosa Or Leber Congenital Amaurosis," *Proc. Natl. Acad. Sci. USA*, 95:3088–3093 (1998), which is hereby incorporated by reference). Although the profound visual deficit early in life is similar in the human and dog, the lack of ophthalmoscopically visible advanced retinal degeneration in adult dogs is not, and may indicate a difference in the temporal course of the photoreceptor disease. After all, most dogs affected with the different forms of PRA show evidence of advanced fundus pathology by 5 years (Parshall et al., "Photoreceptor Dysplasia: An Inherited Progressive Retinal Atrophy Of Miniature Schnauzer Dogs," *Prog. Vet. Comp. Ophthalm.*, 1:187–203 (1991), which is hereby incorporated by reference), an age that would be comparable to a 35 year old human.

Mice with an RPE65 gene knockout have recently been created (Redmond et al., "Characterization Of An RPE65 Knockout Mouse: A Model For Leber's Congenital Amaurosis Type II," *Supp. Inv. Ophthalm. Vis. Sci.*, 39:S643 (1998), which is hereby incorporated by reference). Homozygous mutant mice show irregularities of the rod outer segments by 15 weeks of age, and these changes are associated with a 4.5 log unit increase in the dark adapted threshold, and a small amplitude ERG that is almost identical to that recorded under light adapted conditions. Even though the rod ERG is abolished, the results indicate that the cone ERG is normal. A recent commentary has suggested that the RPE65 gene product functions in retinoid metabolism in the RPE and retina (Wright, "A Searchlight Through The Fog," *Nat. Genet.*, 17:132–134 (1997), which is hereby incorporated by reference). Based on this putative function, the normal cone ERG function in the absence of rod mediated activity could be interpreted as supporting the hypothesis that rod and cones have different and independent pathways for visual pigment regeneration (Jones et al., "Retinoid Requirements For Recovery Of Sensitivity After Visual-Pigment Bleaching In Isolated Photoreceptors," *Proc. Natl. Acad. Sci. USA*, 86:9606–9610 (1989), which is hereby incorporated by reference). This difference, however, does not appear to exist in the dog since cone ERG function was compromised in all dogs with the mutation, and profound impairment of day vision was present in some of the affected animals. This issue merits further investigation as it may play a significant role in the evaluation of mice or dogs following RPE cell transplantation or vector-mediated gene therapy for the experimental treatment of the disease.

The salient pathologic abnormality in the retina of dogs with the 4 nucleotide deletion in the RPE65 gene, documented above or reported previously (Wrigstad et al., "Slowly Progressive Changes Of The Retina And Retinal Pigments Epithelium In Briard Dogs With Hereditary Retinal Dystrophy. A Morphologic Study," *Doc. Ophthalmol.*, 87:337–354 (1994); Wrigstad et al., "Ultrastructural Changes Of The Retina And The Retinal Pigment Epithelium In Briard Dogs With Hereditary Congenital Night Blindness And Partial Day Blindness," *Exp. Eye Res.*, 55:805–818 (1992), which are hereby incorporated by reference), is the accumulation of lipoidal inclusions of variable size within the pigment epithelium. Mice with the RPE65 gene knockout have no rhodopsin in the dark adapted retinal rods, but accumulate all-trans retinyl esters in the pigment epithelium. The accumulation of all-trans retinyl esters in the RPE suggests that the RPE65 protein functions in one of the metabolic steps involved in the conversion of all-trans retinyl esters to 11-cis retinol (Wright, "A Searchlight Through The Fog," *Nat. Genet.*, 17:132–134 (1997), which is hereby incorporated by reference). Although the precise function of the RPE65 protein in RPE retinoid metabolism is still to be determined, deficiency of the protein, either in naturally occurring cases or in transgenic knockout mice, results in the accumulation of all-trans retinyl esters in the RPE. Based on prior studies of vitamin A metabolism in the frog eye, these retinyl esters probably accumulate in oil droplets within the RPE which is the major storage depot for esterified vitamin A in the RPE (Bridges, "Vitamin A And The Role Of The Pigment Epithelium During Bleaching And Regeneration Of Rhodopsin In The Frog Eye," *Exp. Eye Res.*, 22:435–455 (1976), which is hereby incorporated by reference). These lipoidal inclusions are present in the RPE of affected dogs, and their number and size increases with age (Wrigstad et al., "Slowly Progressive Changes Of The Retina And Retinal Pigments Epithelium In Briard Dogs With Hereditary Retinal Dystrophy. A Morphologic Study," *Doc. Ophthalmol.*, 87:337–354 (1994); Wrigstad et al., "Ultrastructural Changes Of The Retina And The Retinal Pigment Epithelium In Briard Dogs With Hereditary Congenital Night Blindness And Partial Day Blindness," *Exp. Eye Res.*, 55:805–818 (1992), which are hereby incorporated by reference; see above).

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for identifying briard dogs which are carriers of or are affected with congenital stationary night blindness, said method comprising:

obtaining a biological sample from a briard dog and testing the biological sample for a gene encoding canine RPE65 comprising a nucleotide sequence according to SEQ ID No. 1 having an AAGA deletion mutation of nucleotides 487 through 490, wherein the presence of the deletion mutation in one or both alleles of the RPE65 gene is indicative of a carrier briard dog or a briard dog affected with congenital stationary night blindness.

2. The method according to claim 1, wherein the mutation in one allele is indicative of a carrier of congenital stationary night blindness.

3. The method according to claim 1, wherein said testing is carried out by an oligonucleotide ligation assay.

4. The method according to claim 1, wherein said testing is carried out by direct sequence analysis.

5. The method according to claim 1, wherein said testing is carried out by subjecting the biological sample to conditions effective to hybridize DNA molecules with the mutation to a probe specific for the sequence of the mutation.

6. The method according to claim 1, wherein said testing is carried out by digesting the biological sample with a restriction endonuclease.

7. The method according to claim 1, wherein said testing is carried out by ligase detection reaction.

8. The method according to claim 1, wherein said testing is carried out by single strand polymorphism assay.

9. The method according to claim 1, wherein said testing is carried out by ligase chain reaction.

10. The method according to claim 1, wherein said testing is carried out by PCR-based restriction fragment length polymorphism.

11. The method according to claim 1, wherein said testing is carried out by performing PCR using genomic DNA templates and polyacrylamide gel electrophoresis.

12. The method according to claim 1, wherein said testing is carried out by Taq cycle sequencing.

13. The method according to claim 1, wherein said testing comprises:

amplifying a region of the gene encoding canine RPE65 to provide an amplified fragment before detecting any mutation present in the biological sample.

14. The method according to claim 1, wherein the nucleotide sequence is a deoxyribonucleic acid.

15. The method according to claim 1, wherein the nucleotide sequence is a messenger ribonucleic acid.

16. The method according to claim 1, wherein the biological sample is any tissue containing genomic DNA.

17. The method according to claim 16, wherein the biological sample is blood, hair, mucosal scrapings, semen, tissue biopsy, or saliva.

* * * * *

UNITED STATES PATENT AND TRADEMARK OFFICE
CERTIFICATE OF CORRECTION

PATENT NO. : 6,428,958 B1
APPLICATION NO. : 09/645370
DATED : August 6, 2002
INVENTOR(S) : Aquirre et al.

It is certified that error appears in the above-identified patent and that said Letters Patent is hereby corrected as shown below:

Col. 1 at lines 8-11, delete "The subject matter of this application was made with support from the United States Government under Grant No. EY 06855 from the National Institutes of Health. The United States Government may retain certain rights." and insert --This invention was made with government support under grant EY 06855 awarded by National Institutes of Health. The government has certain rights in the invention-- in its place.

Signed and Sealed this

Fourteenth Day of April, 2009

JOHN DOLL
*Acting Director of the United States Patent and Trademark Office*

SEQUENCE LISTING

```
<160> NUMBER OF SEQ ID NOS: 8

<210> SEQ ID NO 1
<211> LENGTH: 1724
<212> TYPE: DNA
<213> ORGANISM: Canis familiaris

<400> SEQUENCE: 1
```

-continued

```
cgaccgtctg tcctgccctg ggagacaatg tccatccaag tggagcatcc cgccggcggt      60
tacaagaagc tgtttgaaac cgtggaagag ctgtcgtcgc cgctcaccgc ccacgtgaca     120
ggcaggatcc cgctctggct cacgggcagt ctcctccgat gcggaccggg gctcttcgag     180
gttggatctg aaccatttta ccacctgttt gacggacaag cccttctgca cagttcgac     240
tttaagaag gacacgtcac ctatcacaga aggttcatcc gcaccgatgc ttacgtccgg     300
gcaatgaccg agaaaaggat cgtcataacg gaatttggca cctgtgcgtt cccagatccc     360
tgcaagaata tattttccag gttttttttct tacttccgag gagtggaggt cactgacaat     420
gccctttgtta acgtctaccc agtaggggaa gattactacg cctgcacgga gaccaacttc     480
attacaaaga ttaatcctga daccctggag acaattaagc aggttgatct ctgcaactac     540
gtctctgtca atggagccac cgctcacccc cacattgaaa atgatgggac tgtttacaac     600
attggtaatt gctttgggaa aaattttcg attgcctaca atattgtaaa gatccctcca     660
ctccaagcag acaaggaaga tccaataagc aagtccgagg tcgtcgtaca attcccctgc     720
agcgaccgat tcaagccatc gtacgtccat agttttggtt tgactcccaa ctatattgtt     780
tttgtggaga cgccagtcaa aattaacctg ctcaagttcc tttcttcgtg gagtctttgg     840
ggagccaact acatggattg ttttgagtcc aatgaaacca tggggttttg gcttcacatc     900
gctgacaaaa aagaaaaaa gtatctcaat aataagtaca ggacctcttc ctttaatctc     960
ttccatcata tcaatactta cgaagacaat gagtttctga ttgtggatct ctgctgctgg    1020
aaaggatttg aattcgtcta caattacttg tatttagcca atttacgtga aactgggaa    1080
gaggtgaaaa aaaatgccag aaaggctccg cagcctgaag ttaggagatc cgtgcttcct    1140
ttgaatatcg acaaggccga cacaggcaag aacctagtca ccccttcccaa cacgacggcc    1200
actgcaactc tgcgcagcga cgagaccatc tggctggaac ctgaggttct cttctcaggg    1260
cctcgtcaag ccttttgagtt tcctcaaatc aactatcaga agtatggcgg aagccttac    1320
acgtacgcgt atggacttgg cttgaatcac ttcgttccgg acaggctctg caagctgaac    1380
gtcaagacta agaaacgtg ggtatggcaa gagcccgact catacccatc agaacccatc    1440
tttgtttctc acccagatgc cttggaagaa gatgatggtg tagttctgag tgtggtggtg    1500
agccctgggg caggacaaaa gcctgcttat cttctgattc tgaatgccaa ggatttgagt    1560
gaagttgcca gggctgaagt ggagattaac atccctgtca cctttcatgg actgttcaaa    1620
aaatcctaag tacattctag caaattatat ttctattgac aaagtcaaga aaaagtgagg    1680
tctgcaatca aattctgttc aattttagcc tgctgtatta cagg                     1724
```

<210> SEQ ID NO 2
<211> LENGTH: 533
<212> TYPE: PRT
<213> ORGANISM: Canis familiaris

<400> SEQUENCE: 2

```
Met Ser Ile Gln Val Glu His Pro Ala Gly Gly Tyr Lys Lys Leu Phe
  1               5                  10                  15

Glu Thr Val Glu Glu Leu Ser Ser Pro Leu Thr Ala His Val Thr Gly
             20                  25                  30

Arg Ile Pro Leu Trp Leu Thr Gly Ser Leu Leu Arg Cys Gly Pro Gly
         35                  40                  45

Leu Phe Glu Val Gly Ser Glu Pro Phe Tyr His Leu Phe Asp Gly Gln
     50                  55                  60

Ala Leu Leu His Lys Phe Asp Phe Lys Glu Gly His Val Thr Tyr His
```

-continued

```
             65                  70                  75                  80
Arg Arg Phe Ile Arg Thr Asp Ala Tyr Val Arg Ala Met Thr Glu Lys
                    85                  90                  95
Arg Ile Val Ile Thr Glu Phe Gly Thr Cys Ala Phe Pro Asp Pro Cys
                   100                 105                 110
Lys Asn Ile Phe Ser Arg Phe Phe Ser Tyr Phe Arg Gly Val Glu Val
                   115                 120                 125
Thr Asp Asn Ala Leu Val Asn Val Tyr Pro Val Gly Glu Asp Tyr Tyr
               130                 135                 140
Ala Cys Thr Glu Thr Asn Phe Ile Thr Lys Ile Asn Pro Glu Thr Leu
145                 150                 155                 160
Glu Thr Ile Lys Gln Val Asp Leu Cys Asn Tyr Val Ser Val Asn Gly
                   165                 170                 175
Ala Thr Ala His Pro His Ile Glu Asn Asp Gly Thr Val Tyr Asn Ile
                   180                 185                 190
Gly Asn Cys Phe Gly Lys Asn Phe Ser Ile Ala Tyr Asn Ile Val Lys
               195                 200                 205
Ile Pro Pro Leu Gln Ala Asp Lys Glu Asp Pro Ile Ser Lys Ser Glu
               210                 215                 220
Val Val Val Gln Phe Pro Cys Ser Asp Arg Phe Lys Pro Ser Tyr Val
225                 230                 235                 240
His Ser Phe Gly Leu Thr Pro Asn Tyr Ile Val Phe Val Glu Thr Pro
                   245                 250                 255
Val Lys Ile Asn Leu Leu Lys Phe Leu Ser Ser Trp Ser Leu Trp Gly
                   260                 265                 270
Ala Asn Tyr Met Asp Cys Phe Glu Ser Asn Glu Thr Met Gly Val Trp
                   275                 280                 285
Leu His Ile Ala Asp Lys Lys Arg Lys Lys Tyr Leu Asn Asn Lys Tyr
               290                 295                 300
Arg Thr Ser Ser Phe Asn Leu Phe His His Ile Asn Thr Tyr Glu Asp
305                 310                 315                 320
Asn Glu Phe Leu Ile Val Asp Leu Cys Cys Trp Lys Gly Phe Glu Phe
                   325                 330                 335
Val Tyr Asn Tyr Leu Tyr Leu Ala Asn Leu Arg Glu Asn Trp Glu Glu
                   340                 345                 350
Val Lys Lys Asn Ala Arg Lys Ala Pro Gln Pro Glu Val Arg Arg Ser
                   355                 360                 365
Val Leu Pro Leu Asn Ile Asp Lys Ala Asp Thr Gly Lys Asn Leu Val
               370                 375                 380
Thr Leu Pro Asn Thr Thr Ala Thr Ala Thr Leu Arg Ser Asp Glu Thr
385                 390                 395                 400
Ile Trp Leu Glu Pro Glu Val Leu Phe Ser Gly Pro Arg Gln Ala Phe
                   405                 410                 415
Glu Phe Pro Gln Ile Asn Tyr Gln Lys Tyr Gly Gly Lys Pro Tyr Thr
                   420                 425                 430
Tyr Ala Tyr Gly Leu Gly Leu Asn His Phe Val Pro Asp Arg Leu Cys
                   435                 440                 445
Lys Leu Asn Val Lys Thr Lys Glu Thr Trp Val Trp Gln Glu Pro Asp
450                 455                 460
Ser Tyr Pro Ser Glu Pro Ile Phe Val Ser His Pro Asp Ala Leu Glu
465                 470                 475                 480
Glu Asp Asp Gly Val Val Leu Ser Val Val Ser Pro Gly Ala Gly
                   485                 490                 495
```

```
Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
            515                 520                 525

Leu Phe Lys Lys Ser
        530

<210> SEQ ID NO 3
<211> LENGTH: 205
<212> TYPE: PRT
<213> ORGANISM: Canis familiaris

<400> SEQUENCE: 3

Met Ser Ile Gln Val Glu His Pro Ala Gly Gly Tyr Lys Lys Leu Phe
  1               5                  10                  15

Glu Thr Val Glu Glu Leu Ser Ser Pro Leu Thr Ala His Val Thr Gly
             20                  25                  30

Arg Ile Pro Leu Trp Leu Thr Gly Ser Leu Leu Arg Cys Gly Pro Gly
         35                  40                  45

Leu Phe Glu Val Gly Ser Glu Pro Phe Tyr His Leu Phe Asp Gly Gln
     50                  55                  60

Ala Leu Leu His Lys Phe Asp Phe Lys Glu Gly His Val Thr Tyr His
 65                  70                  75                  80

Arg Arg Phe Ile Arg Thr Asp Ala Tyr Val Arg Ala Met Thr Glu Lys
                 85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
            115                 120                 125

Thr Asp Asn Ala Leu Val Asn Val Tyr Pro Val Gly Glu Asp Tyr Tyr
            130                 135                 140

Ala Cys Thr Glu Thr Asn Phe Ile Thr Leu Ile Leu Arg Pro Trp Arg
145                 150                 155                 160

Gln Leu Ser Arg Leu Ile Ser Ala Thr Thr Leu Ser Met Glu Pro
            165                 170                 175

Pro Leu Thr Pro Thr Leu Lys Met Met Gly Leu Phe Thr Leu Val
            180                 185                 190

Ile Ala Leu Gly Lys Ile Phe Arg Leu Pro Thr Ile Leu
            195                 200                 205

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: forward
      primer

<400> SEQUENCE: 4 caatgcccctt gttaatgtct acccag                                          26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: reverse
      primer
```

-continued

```
<400> SEQUENCE: 5
cctgcttaat tgtctccaag gtctc                                            25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:  vector
      specific reverse primer

<400> SEQUENCE: 6
ccgctctaga agtactctcg agtt                                             24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:  vector
      specific forward primer

<400> SEQUENCE: 7
ggtcgacact agtggatcca aag                                              23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:  reverse
      primer

<400> SEQUENCE: 8
tgcttgctca actcagtgct ttctg                                            25
```